US009090948B2

(12) United States Patent
Abravaya et al.

(10) Patent No.: US 9,090,948 B2
(45) Date of Patent: Jul. 28, 2015

(54) PRIMERS AND PROBES FOR DETECTING HUMAN PAPILLOMAVIRUS AND HUMAN BETA GLOBIN SEQUENCES IN TEST SAMPLES

(75) Inventors: Klara Abravaya, Kenilworth, IL (US);
Brian J. Erickson, Kenosha, WI (US);
Shihai X. Huang, Evanston, IL (US);
Wai-Bing X. Mak, Cary, IL (US); John A. Salituro, Union Grove, WI (US);
Ning Tang, Libertyville, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 1040 days.

(21) Appl. No.: 12/241,119

(22) Filed: Sep. 30, 2008

(65) Prior Publication Data
US 2010/0081124 A1    Apr. 1, 2010

(51) Int. Cl.
*C12Q 1/70* (2006.01)
*C12Q 1/68* (2006.01)

(52) U.S. Cl.
CPC .............. *C12Q 1/708* (2013.01); *C12Q 1/6886* (2013.01); *C12Q 2600/112* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,849,332 A | 7/1989 | Lorincz | |
| 4,889,818 A | 12/1989 | Gelfand et al. | |
| 5,130,238 A | 7/1992 | Malek et al. | |
| 5,185,439 A | 2/1993 | Arnold, Jr. et al. | |
| 5,210,015 A | 5/1993 | Gelfand et al. | |
| 5,234,809 A | 8/1993 | Boom et al. | |
| 5,270,184 A | 12/1993 | Walker et al. | |
| 5,310,652 A | 5/1994 | Gelfand et al. | |
| 5,322,770 A | 6/1994 | Gelfand | |
| 5,344,166 A | 9/1994 | Fink | |
| 5,364,758 A | 11/1994 | Meijer et al. | |
| 5,399,491 A | 3/1995 | Kacian et al. | |
| 5,445,166 A | 8/1995 | Taylor | |
| 5,487,792 A | 1/1996 | King et al. | |
| 5,585,481 A | 12/1996 | Arnold, Jr. et al. | |
| 5,705,627 A | 1/1998 | Manos et al. | |
| 5,804,375 A | 9/1998 | Gelfand et al. | |
| 5,846,726 A | 12/1998 | Nadeau et al. | |
| 5,925,517 A | 7/1999 | Tyagi et al. | |
| 6,214,979 B1 | 4/2001 | Gelfand et al. | |
| 6,235,504 B1 | 5/2001 | Zhang et al. | |
| 6,265,154 B1 * | 7/2001 | Kroeger et al. | 435/6 |
| 6,277,581 B1 | 8/2001 | O'Brien et al. | |
| 6,352,825 B1 * | 3/2002 | Meijer et al. | 435/5 |
| 6,482,588 B1 * | 11/2002 | Van Doorn et al. | 435/5 |
| 7,198,893 B1 * | 4/2007 | Koster et al. | 435/6 |
| 2004/0253584 A1 * | 12/2004 | Ihle et al. | 435/6 |
| 2005/0069887 A1 * | 3/2005 | Kitabayashi et al. | 435/6 |

FOREIGN PATENT DOCUMENTS

| | | |
|---|---|---|
| EA | 005739 | 6/2005 |
| EA | 006975 | 6/2006 |
| EP | 0477972 A2 | 4/1992 |
| EP | 0500224 A2 | 8/1992 |
| EP | 1302550 A1 | 4/2003 |
| RU | 2228355 | 5/2004 |
| WO | 9522626 A1 | 8/1995 |
| WO | 9817829 A2 | 4/1998 |
| WO | 9914377 A2 | 3/1999 |
| WO | 99/63118 | 12/1999 |
| WO | 01/75174 | 10/2001 |
| WO | 0186001 A1 | 11/2001 |
| WO | 03/057914 | 7/2003 |
| WO | 03076667 A1 | 9/2003 |
| WO | 2007100198 A1 | 9/2007 |
| WO | WO 2007100198 A1 * | 9/2007 |
| WO | 2008017162 A1 | 2/2008 |
| WO | WO 2008017162 A1 * | 2/2008 |

OTHER PUBLICATIONS

Chew et al. Human papillomavirus 16 infection in adenocarcinoma of the cervix. British Journal of Cancer (2005) 93: 1301-1304.*
He et al. BioTechniques (1994) 17(1): 82 and 84-86.*
Buck et al. Design strategies and performance of custom DNA sequencing primers. BioTechniques 1999;27:528-36.*
International Search Report and Written Opinion for Application No. PCT/US2009/058992, mailed on Jun. 21, 2010, 23 pages.
Lawn R.M., et al., "The Nucleotide Sequence of the Human Beta-globin Gene.," Cell, 1980, vol. 21 (3), pp. 647-651.
Andras S.C., et al., "Strategies for Signal Amplification in Nucleic Acid Detection.," Molecular Biotechnology, 2001, vol. 19 (1), pp. 29-44.
Bayer E.A., et al., ""The Use of the Avidin-Biotin Complex as a Tool in Molecular Biology. ,"" Methods and Biochemical Analysis, 1980, vol. 26, pp. 1-45.
Belousov E.S., et al., "Sequence-specific Targeting and Covalent Modification of Human Genomic Dna.," Nucleic Acids Research, 1997, vol. 25 (17), pp. 3440-3444.
Berry D.J., et al., "A Laboratory and Clinical Evaluation of an Immunochemiluminometric Assay of Thyrotropin in Serum.," Clinical Chemistry, 1988, vol. 34 (10), pp. 2087-2090.
Brigati D.J., et al., "Detection of Viral Genomes in Cultured Cells and Paraffin-Embedded Tissue Sections Using Biotin-Labeled Hybridization Probes," Virology, 1983, vol. 126 (1), pp. 32-50.

(Continued)

*Primary Examiner* — Suchira Pande
(74) *Attorney, Agent, or Firm* — Lisa V. Mueller; Michael Best & Friedrich LLP

(57) ABSTRACT

The present invention relates to primers, probes, primer sets, primer and probe sets, methods and kits for detecting human papillomaviruses, human beta globin sequences and human papillomaviruses and human beta globin sequences in a test sample.

5 Claims, 6 Drawing Sheets

(56) References Cited

OTHER PUBLICATIONS

Broker T.R., et al., "Electron Microscopic Visualization of TRNA Genes with Ferritin-avidin: Biotin Labels," Nucleic Acids Research, 1978, vol. 5 (2), pp. 363-384.

Brown E.L., et al., "Chemical Synthesis and Cloning of a Tyrosine TRNA Gene," Methods in Enzymology, 1979, vol. 68, pp. 109-151.

Chan A.B., et al., "NASBA and Other Transcription-based Amplification Methods for Research and Diagnostic Microbiology," Reviews in Medical Microbiology, 1999, vol. 10 (4), pp. 185-196.

Compton J., "Nucleic Acid Sequence-Based Amplification," Nature, 1991, vol. 350 (6313), pp. 91-92.

Connolly B.A., et al., "Chemical Synthesis of Oligonucleotides Containing a Free Sulphydryl Group and Subsequent Attachment of Thiol Specific Probes," Nucleic Acids Research, 1985, vol. 13 (12), pp. 4485-4502.

Ezaki et al., "Papillomaviridae DnaJ PCR Primer, SEQ ID 340", EBI, Apr. 10, 2008.

Fahy E., et al., "Self-sustained Sequence Replication (3sr): An Isothermal Transcription-based Amplification System Alternative to Pcr.," Pcr Methods and Applications, 1991, vol. 1 (1), pp. 25-33.

Giachetti C., et al., "Highly Sensitive Multiplex Assay for Detection of Human Immunodeficiency Virus Type 1 and Hepatitis C Virus Rna.," Journal of Clinical Microbiology, 2002, vol. 40 (7), pp. 2408-2419.

Guatelli J.C., et al., "Isothermal, in Vitro Amplification of Nucleic Acids By A Multienzyme Reaction Modeled after Retroviral Replication.," Proceedings of the National Academy of Sciences of the United States of America, 1990, vol. 87 (5), pp. 1874-1878.

He Q., et al., "Primers are Decisive for Sensitivity of Pcr.," Biotechniques, 1994, vol. 17 (1), pp. 82-87.

Holland P.M., et al., "Detection of Specific Polymerase Chain Reaction Product by Utilizing the 5'—3' Exonuclease Activity of Thermus Aquaticus DNA Polymerase," Proceedings of the National Academy of Sciences, 1991, vol. 88 (16), pp. 7276-7280.

Hopman A.H., et al., "Mercurated Nucleic Acid Probes, A New Principle for Non-radioactive in Situ Hybridization," Experimental Cell Research, 1987, vol. 169 (2), pp. 357-368.

Joos S., et al., "Mapping and Chromosome Analysis: the Potential of Fluorescence in Situ Hybridization," Journal of Biotechnology, 1994, vol. 35 (2-3), pp. 135-153.

Kievits T., et al., "NASBA Isothermal Enzymatic in Vitro Nucleic Acid Amplification Optimized for the Diagnosis of HIV-1 Infection," Journal of Virological Methods, 1991, vol. 35 (3), pp. 273-286.

Kimmel A.R., et al., "Preparation of Cdna and the Generation of Cdna Libraries: Overview.," Methods in Enzymology, 1987, vol. 152, pp. 307-316.

Kleter B., et al., "Novel Short-fragment Pcr Assay for Highly Sensitive Broad-spectrum Detection of Anogenital Human Papillomaviruses.," The American Journal of Pathology, 1998, vol. 153 (6), pp. 1731-1739.

Kostrikis L.G., et al., "Spectral Genotyping of Human Alleles.," Science, 1998, vol. 279 (5354), pp. 1228-1229

Kricka L.J., et al., "Stains, Labels and Detection Strategies for Nucleic Acids Assays," Annals of Clinical Biochemistry, 2002, vol. 39 (Pt 2), pp. 114-129.

Kwoh D.Y., et al., "Transcription-Based Amplification System and Detection of Amplified Human Immunodeficiency Viru: Type 1 with a Bead-Based Sandwixh Hybridization Format," Proceeding of the National Academy of Sciences of the USA, 1989, vol. 86 (4), pp. 1173-1177.

Landegent J.E., et al., "2-Acetylaminofluorene-modified Probes for the Indirect Hybridocytochemical Detection of Specific Nucleic Acid Sequences," Experimental Cell Research, 1984, vol. 153 (1), pp. 61-72.

Langer P.R., et al., "Enzymatic Synthesis of Biotin-Labeled Polynucleotides: Novel Nucleic Acid Affinity Probes," Proceedings of the National Academy of Sciences, 1981, vol. 78 (11), pp. 6633-6637.

Mansfield E.S., et al., "Nucleic Acid Detection Using Non-radioactive Labelling Methods.," Molecular and Cellular Probes, 1995, vol. 9 (3), pp. 145-156.

Marras S.A., et al., "Multiplex Detection of Single-nucleotide Variations Using Molecular Beacons," Genetic Analysis , 1999, vol. 14 (5-6), pp. 151-156.

Maxam A.M., et al., "Sequencing End-labeled Dna with Base-specific Chemical Cleavages," Methods in Enzymology, 1980, vol. 65 (1), pp. 499-560.

McFarland G.D., et al., "Separation of Oligo-rna by Reverse-phase Hplc," Nucleic Acids Research, 1979, vol. 7 (4), pp. 1067-1080.

Narang S.A., et al., "Improved Phosphotriester Method for the Synthesis of Gene Fragments," Methods in Enzymology, 1979, vol. 68, pp. 90-98.

Pearson J.D., et al., "High-performance Anion-exchange Chromatography of Oligonucleotides," Journal of Chromatography, 1983, vol. 255, pp. 137-149.

Pieles U., et al., "Matrix-assisted Laser Desorption Ionization Time-of-flight Mass Spectrometry: A Powerful Tool for the Mass and Sequence Analysis of Natural and Modified Oligonucleotides.," Nucleic Acids Research, 1993, vol. 21 (14), pp. 3191-3196.

Richardson R.W., et al., "Biotin and Fluorescent Labeling of RNA using T4 RNA Ligase," Nucleic Acids Research, 1983, vol. 11 (18), pp. 6167-6184.

Sabol I., et al., "Evaluation of Different Techniques for Identification of Human Papillomavirus Types of Low Prevalence.," Journal of Clinical Microbiology, 2008, vol. 46 (5), pp. 1606-1613.

Saiki R.K., et al., "Analysis of Enzymatically Amplified-Globin and HLA-DQ" DNA with Allele-Specific Oligonucleotide Probes, Nature, 1986, vol. 324 (6093), pp. 163-166.

Schmitt M., et al., "Homogeneous Amplification of Genital Human Alpha Papillomaviruses by Pcr Using Novel Broad-spectrum Gp5+ and Gp6+ Primers.," Journal of Clinical Microbiology, 2008, vol. 46 (3), pp. 1050-1059.

Smith L.M., et al., "The Synthesis of Oligonucleotides Containing an Aliphatic Amino Group at the 5" Terminus: Synthesis of Fluorescent DNA Primers for use in DNA Sequence Analysis, Nucleic Acids Research, 1985, vol. 13 (7), pp. 2399-2412.

Sokol D.L., et al., "Real Time Detection of Dna.Rna Hybridization in Living Cells.," Proceedings of the National Academy of Sciences of the United States of America, 1998, Vol. 95 (20), pp. 11538-11543.

Tchen P., et al., "Chemically Modified Nucleic Acids as Immunodetectable Probes in Hybridization Experiments," Proceedings of the National Academy of Sciences, 1984, vol. 81 (11), pp. 3466-3470.

Temsamani J., et al., "Enzymatic Labeling of Nucleic Acids.," Molecular Biotechnology, 1996, vol. 5 (3), pp. 223-232.

Tyagi S., et al., "Molecular Beacons: Probes that Fluoresce Upon Hybridization," Nature Biotechnology, 1996, vol. 14 (3), pp. 303-308.

Tyagi S., et al., "Multicolor Molecular Beacons for Allele Discrimination," Nature Biotechnology, 1998, vol. 16 (1), pp. 49-53.

Van Gijlswijk R.P., et al., "Universal Linkage System: Versatile Nucleic Acid Labeling Technique.," Expert Review of Molecular Diagnostics, 2001, vol. 1 (1), pp. 81-91.

Walker G.T., et al., "Isothermal in Vitro Amplification of DNA by a Restriction Enzyme/DNA Polymerase System," Proceedings of the National Academy of Sciences, 1992, vol. 89 (1) pp. 392-396.

Weeks., et al., "Acridinium esters as high-specific-activity labels in immunoassay", Clin Chem. 1983, 29(8), 1474-1479.

Wu H., et al., "Improved Oligonucleotide Sequencing by Alkaline Phosphatase and Exonuclease Digestions with Mass Spectrometry," Analytical Biochemistry, 2001, vol. 290 (2), pp. 347-352.

Genbank Accession No. U45917.1, Human papillomavirus type 51, isolate T273, major capsid protein L1 (L1) gene, partial cds. (1996).

* cited by examiner

SEQUENCE LISTING

<160> NUMBER OF SEQ ID NOS: 24

<210> SEQ ID NO 1
<211> LENGTH: 25
<212> TYPE: DNA
<213> ORGANISM: Artificial sequence
<220> FEATURE:
<223> OTHER INFORMATION: Chemically synthesized

<400> SEQUENCE: 1
tatttgttac tgtggtagat actac                                    25

<210> SEQ ID NO 2
<211> LENGTH: 29
<212> TYPE: DNA
<213> ORGANISM: Artificial sequence
<220> FEATURE:
<223> OTHER INFORMATION: Chemically synthesized

<400> SEQUENCE: 2
caattgtttg ttactgttgt ggatactac                                29

<210> SEQ ID NO 3
<211> LENGTH: 25
<212> TYPE: DNA
<213> ORGANISM: Artificial sequence
<220> FEATURE:
<223> OTHER INFORMATION: Chemically synthesized

<400> SEQUENCE: 3
tttttattac ctgtgttgat actac                                    25

<210> SEQ ID NO 4
<211> LENGTH: 28
<212> TYPE: DNA
<213> ORGANISM: Artificial sequence
<220> FEATURE:
<223> OTHER INFORMATION: Chemically synthesized

<400> SEQUENCE: 4
gaaaaataaa ctgtaaatca tattcctc                                 28

<210> SEQ ID NO 5
<211> LENGTH: 28
<212> TYPE: DNA
<213> ORGANISM: Artificial sequence
<220> FEATURE:
<223> OTHER INFORMATION: Chemically synthesized

<400> SEQUENCE: 5
gaaaaataaa ttgcaattca tactcttc                                 28

<210> SEQ ID NO 6
<211> LENGTH: 22
<212> TYPE: DNA
<213> ORGANISM: Artificial sequence
<220> FEATURE:
<223> OTHER INFORMATION: Chemically synthesized

<400> SEQUENCE: 6
ggcaggttgg tatcaaggtt ac                                       22

<210> SEQ ID NO 7
<211> LENGTH: 22
<212> TYPE: DNA
<213> ORGANISM: Artificial sequence

```
<220> FEATURE:
<223> OTHER INFORMATION: Chemically synthesized

<400> SEQUENCE: 7
cctaagggtg ggaaaataga cc                                              22

<210> SEQ ID NO 8
<211> LENGTH: 22
<212> TYPE: DNA
<213> ORGANISM: Artificial sequence
<220> FEATURE:
<223> OTHER INFORMATION: Chemically synthesized

<400> SEQUENCE: 8
atgtgctgcc atatctactt ca                                              22

<210> SEQ ID NO 9
<211> LENGTH: 22
<212> TYPE: DNA
<213> ORGANISM: Artificial sequence
<220> FEATURE:
<223> OTHER INFORMATION: Chemically synthesized

<400> SEQUENCE: 9
cacagtctcc tgtacctggg ca                                              22

<210> SEQ ID NO 10
<211> LENGTH: 22
<212> TYPE: DNA
<213> ORGANISM: Artificial sequence
<220> FEATURE:
<223> OTHER INFORMATION: Chemically synthesized

<400> SEQUENCE: 10
taaaagtagt aattttaaag ag                                              22

<210> SEQ ID NO 11
<211> LENGTH: 19
<212> TYPE: DNA
<213> ORGANISM: Artificial sequence
<220> FEATURE:
<223> OTHER INFORMATION: Chemically synthesized

<400> SEQUENCE: 11
atgcacacaa gtaactagt                                                  19

<210> SEQ ID NO 12
<211> LENGTH: 19
<212> TYPE: DNA
<213> ORGANISM: Artificial sequence
<220> FEATURE:
<223> OTHER INFORMATION: Chemically synthesized

<400> SEQUENCE: 12
ctgtgtgttc tgctgtgtc                                                  19

<210> SEQ ID NO 13
<211> LENGTH: 14
<212> TYPE: DNA
<213> ORGANISM: Artificial sequence
<220> FEATURE:
<223> OTHER INFORMATION: Chemically synthesized

<400> SEQUENCE: 13
tccatacctt ctac                                                       14
```

```
<210> SEQ ID NO 14
<211> LENGTH: 22
<212> TYPE: DNA
<213> ORGANISM: Artificial sequence
<220> FEATURE:
<223> OTHER INFORMATION: Chemically synthesized

<400> SEQUENCE: 14
cctactaagt ttaagcagta ta                                              22

<210> SEQ ID NO 15
<211> LENGTH: 19
<212> TYPE: DNA
<213> ORGANISM: Artificial sequence
<220> FEATURE:
<223> OTHER INFORMATION: Chemically synthesized

<400> SEQUENCE: 15
ttagcactgc cactgctgc                                                  19

<210> SEQ ID NO 16
<211> LENGTH: 14
<212> TYPE: DNA
<213> ORGANISM: Artificial sequence
<220> FEATURE:
<223> OTHER INFORMATION: Chemically synthesized

<400> SEQUENCE: 16
aaaaaggaaa gcac                                                       14

<210> SEQ ID NO 17
<211> LENGTH: 19
<212> TYPE: DNA
<213> ORGANISM: Artificial sequence
<220> FEATURE:
<223> OTHER INFORMATION: Chemically synthesized

<400> SEQUENCE: 17
ctacagaaca gttaagtaa                                                  19

<210> SEQ ID NO 18
<211> LENGTH: 14
<212> TYPE: DNA
<213> ORGANISM: Artificial sequence
<220> FEATURE:
<223> OTHER INFORMATION: Chemically synthesized

<400> SEQUENCE: 18
atgcactgaa gtaa                                                       14

<210> SEQ ID NO 19
<211> LENGTH: 24
<212> TYPE: DNA
<213> ORGANISM: Artificial sequence
<220> FEATURE:
<223> OTHER INFORMATION: Chemically synthesized

<400> SEQUENCE: 19
attcctaatg tatacacacc tacc                                            24

<210> SEQ ID NO 20
<211> LENGTH: 22
<212> TYPE: DNA
<213> ORGANISM: Artificial sequence
<220> FEATURE:
<223> OTHER INFORMATION: Chemically synthesized
```

```
<400> SEQUENCE: 20
caatcaatac cttcgccatg tg                                          22

<210> SEQ ID NO 21
<211> LENGTH: 19
<212> TYPE: DNA
<213> ORGANISM: Artificial sequence
<220> FEATURE:
<223> OTHER INFORMATION: Chemically synthesized

<400> SEQUENCE: 21
ctttgtctac tactactga                                              19

<210> SEQ ID NO 22
<211> LENGTH: 20
<212> TYPE: DNA
<213> ORGANISM: Artificial sequence
<220> FEATURE:
<223> OTHER INFORMATION: Chemically synthesized

<400> SEQUENCE: 22
actgggcatg tggagacaga                                             20

<210> SEQ ID NO 23
<211> LENGTH: 23
<212> TYPE: DNA
<213> ORGANISM: Artificial sequence
<220> FEATURE:
<223> OTHER INFORMATION: Chemically synthesized

<400> SEQUENCE: 23
tttgttactg tggtagatac tac                                         23

<210> SEQ ID NO 24
<211> LENGTH: 25
<212> TYPE: DNA
<213> ORGANISM: Artificial sequence
<220> FEATURE:
<223> OTHER INFORMATION: Chemically synthesized

<400> SEQUENCE: 24
gaaaaataaa ctgtaaatca tattc                                       25
```

PRIMERS AND PROBES FOR DETECTING HUMAN PAPILLOMAVIRUS AND HUMAN BETA GLOBIN SEQUENCES IN TEST SAMPLES

RELATED APPLICATION INFORMATION

None.

TECHNICAL FIELD

The present invention relates to primers, probes, primer sets, primer and probe sets, methods and kits for detecting human papillomaviruses, human beta globin sequences and human papillomaviruses and human beta globin sequences in a test sample.

BACKGROUND

Papillomaviruses are DNA viruses that infect the skin and mucous membranes of humans and animals. Approximately 130 types of human papillomaviruses (HPV) have been identified, of which between 30-40 types are transmitted through sexual contact and infect the anogenital region. Some of these HPV types cause genital warts, while others do not cause any noticeable signs of infection. At least 14 HPV types have been associated with a high risk for cervical cancer, namely types 16, 18, 31, 33, 35, 39, 45, 51, 52, 56, 58, 59, 66 and 68. Detection of these high risk types of HPV is important in the prevention of cervical cancer.

The genome of all HPV types is similarly organized. A number of early (E) and late (L) proteins are specifically encoded. E1 and E2 proteins are required for DNA replication. E4 and E5 proteins are required for replication of the viral genome in the upper layers of the epithelium. E6 and E7 proteins are oncogenic and cooperate to immortalize cells and to induce genomic instability. L1 and L2 proteins form the viral capsid and are expressed late in infection in the upper layers of the epithelium. Another part of the genome, namely the long-control-region (LCR), contains most of the regulatory DNA sequences needed for proper replication of the viral genome and expression of the viral genes.

A variety of methods for detecting high risk types of HPV have been devised. Many rely on the detection of unique sequences in the HPV genome. For example, DNA or RNA probes complementary to a portion of the genes of HPV type 35, have been described, such as in U.S. Pat. No. 4,849,332, as useful in screening for the presence of this type of HPV in test samples. Additional probe sequences useful for detecting oncogenic HPV types are disclosed in U.S. Pat. No. 6,265, 154. U.S. Pat. No. 5,705,627 teaches the use of polymerase chain reaction (PCR) to amplify and detect HPV DNA using degenerate or mixed consensus primers, followed by typing using a mixture of genotype-specific DNA probes. Other examples of using consensus primers can be found in U.S. Pat. No. 5,364,758 and Kleter, B. et al., *Am. J. of Pathology*, 1998, 153(6):1731-39. Moreover, many of the methods known in the art also involve detecting human beta globin sequences in test samples.

As illustrated above, a variety of methods for detecting high risk types of HPV are known in the art. Despite such methods, there exists a need in the art for new methods that: (1) are capable of detecting multiple HPV genotypes in a single reaction while at the same time differentiating the detection of certain specific genotypes from others (e.g., partial genotyping); (2) do not exhibit any cross-reactivity between HPV types; (3) provide a robust clinical sensitivity and specificity; and (4) provide high throughput and efficient workflow.

SUMMARY

In one embodiment, the present invention relates to a primer for amplifying human papillomavirus (HPV) types 16, 18, 31, 33, 35, 39, 45, 51, 52, 56, 58, 59, 66 and 68 in a test sample. The primer has a sequence selected from the group consisting of: SEQ ID NO:1, SEQ ID NO:2, SEQ ID NO:3, SEQ ID NO:4, SEQ ID NO:5 and complements thereof.

In another embodiment, the present invention relates to a probe for detecting HPV types 16, 18, 31, 35, 39, 45, 51, 52, 58, 59 or 66 in a test sample. The probe has a sequence selected from the group consisting of: SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:18, SEQ ID NO:19, SEQ ID NO:20 and complements thereof.

In yet another embodiment, the present invention relates to a primer for amplifying a human beta globin sequence in a test sample. The primer has a sequence of SEQ ID NO:6, SEQ ID NO:7, a complement of SEQ ID NO:6, a complement of SEQ ID NO:7 or any combinations thereof.

In still yet another embodiment, the present invention relates to a probe for detecting a human beta globin sequence in a test sample. The probe has a sequence of SEQ ID NO:22 or a complement thereof.

In still yet a further embodiment, the present invention relates to a primer set for amplifying HPV types 16, 18, 31, 33, 35, 39, 45, 51, 52, 56, 58, 59, 66 and 68 in a test sample. The primer set comprises the following:
(a) at least one forward primer having a sequence selected from the group consisting of: SEQ ID NO:1, SEQ ID NO:2, SEQ ID NO:3, complements thereof and any combinations thereof; and
(b) at least one reverse primer having a sequence selected from the group consisting of: SEQ ID NO:4, SEQ ID NO:5, complements thereof and any combinations thereof.

Specifically, the above described primer set can comprise forward primers having the sequence of: SEQ ID NO:1, SEQ ID NO:2 and SEQ ID NO:3 or complements thereof. The above primer set can comprise reverse primers having the sequence of: SEQ ID NO:4 and SEQ ID NO:5 or complements thereof. Alternatively, the primer set can comprise forward primers having the sequence of: SEQ ID NO:1, SEQ ID NO:2 and SEQ ID NO:3 or complements thereof and reverse primers having the sequence of: SEQ ID NO:4 and SEQ ID NO:5 or complements thereof.

In still yet another embodiment, the present invention relates to a primer and probe set for detecting HPV types 16, 18, 31, 33, 35, 39, 45, 51, 52, 56, 58, 59, 66 and 68 in a test sample. The primer and probe set comprises:
(a) three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof; and
(b) fourteen probes having a sequence of: SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof.

In yet a further embodiment, the present invention relates to a primer and probe set for detecting human beta globin in a test sample. The primer and probe set comprises:
(a) a forward primer having a sequence of SEQ ID NO: 6 or a complement thereof and a reverse primer having a sequence of SEQ ID NO:7 or a complement thereof; and
(b) a probe having a sequence of SEQ ID NO:22 or a complement thereof.

In still yet a further embodiment, the present invention relates to a method for detecting one or more of HPV types 16, 18, 31, 33, 35, 39, 45, 51, 52, 56, 58, 59, 66 and 68 in a test sample. The method comprising the steps of:
(a) contacting the test sample with three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof under amplification conditions to generate a first target sequence; and
(b) detecting hybridization between the first target sequence and at least one probe as an indication of the presence of one or more of HPV types 16, 18, 31, 33, 35, 39, 45, 51, 52, 56, 58, 59, 66 and 68 in the test sample, wherein the probe has a sequence of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof.

In the above described method, the amplification conditions comprise submitting the test sample to an amplification reaction carried out in the presence of suitable amplification reagents. Additionally, the amplification reaction can comprise using PCR, real-time PCR (such as, but not limited to, a quantitative PCR assay (e.g., sold under TAQMAN) or reverse-Transcriptase PCR (RT-PCR).

In the above described method, at least one probe is labeled with a detectable label. As is known in the art, the detectable label can be directly attached to at least one probe. Alternatively, the detectable label can be indirectly attached to at least one probe. Moreover, the detectable label can be directly detectable. Alternatively, the detectable label can be indirectly detectable. For example, the detectable label can comprise a fluorescent moiety attached at the 5' end of at least one probe. Moreover, at least one probe can further comprise a quencher moiety attached at its 3' end.

In addition, the above described method can further comprise the steps of:
(a) contacting the test sample with a forward primer having a sequence of SEQ ID NO: 6 or a complement thereof and a reverse primer having a sequence of SEQ ID NO:7 or a complement thereof under amplification conditions to generate a second target sequence; and
(b) detecting hybridization between the second target sequence and the probe having a sequence of SEQ ID NO:22 or a complement thereof as an indication of the presence of a human beta globin in the test sample.

In still yet another embodiment, the present invention relates to a method for detecting and/or differentiating HPV types 16, 18 or both HPV types 16 and 18 in a test sample. The method comprises the steps of:
(a) contacting the test sample with three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof under amplification conditions to generate a first target sequence; and
(b) detecting hybridization between the first target sequence and the following:
 (i) a first probe having a sequence of SEQ ID NO:8 or a complement thereof as an indication of the presence of HPV type 16, wherein said first probe is labeled with a first detectable label;
 (ii) a second probe having a sequence of SEQ ID NO:9 or a complement thereof as an indication of the presence of HPV type 18, wherein said second probe is labeled with a second detectable label, and further wherein the second detectable label is a different detectable label than the first detectable label;
 (iii) one or more additional probes having a sequence of: SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof as an indication of the presence of HPV types 31, 33, 35, 39, 45, 51, 52, 56, 58, 59, 66 or 68, wherein each of the one or more additional probes is labeled with an identical third detectable label and further wherein said third detectable label is a different detectable label than the first detectable label and the second detectable label.

In the above described method the amplification conditions comprise submitting the test sample to an amplification reaction carried out in the presence of suitable amplification reagents. Additionally, the amplification reaction can comprise using PCR, real-time PCR (such as, but not limited to, a quantitative PCR assay (e.g., sold under TAQMAN) or RT-PCR.

In yet another embodiment, the present invention relates to a method for detecting human beta globin in a test sample. The method comprises the steps of:
(a) contacting the test sample with a forward primer having a sequence of SEQ ID NO: 6 or a complement thereof and a reverse primer having a sequence of SEQ ID NO:7 or a complement thereof under amplification conditions to generate a first target sequence; and
(b) detecting hybridization between the first target sequence and the probe having a sequence of SEQ ID NO:22 or a complement thereof as an indication of the presence of a human beta globin in the test sample.

In the above described method the amplification conditions comprise submitting the test sample to an amplification reaction carried out in the presence of suitable amplification reagents. Additionally, the amplification reaction can comprise using PCR, real-time PCR (such as, but not limited to, a quantitative PCR assay (e.g., sold under TAQMAN) or RT-PCR.

In the above described method, at least one probe is labeled with a detectable label. The detectable label can be directly attached to at least one probe. Alternatively, the detectable label can be indirectly attached to at least one probe. Moreover, the detectable label can be directly detectable. Alternatively, the detectable label can be indirectly detectable. For example, the detectable label can comprise a fluorescent moiety attached at the 5' end of at least one probe. Moreover, at least one probe can further comprise a quencher moiety attached at its 3' end.

In addition, the above described method can further comprise the steps of:
(a) contacting the test sample with three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof under amplification conditions to generate a second target sequence; and (b) detecting hybridization between the second target sequence and at least one probe having a sequence of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complement thereof as an indication of the presence of one or more of HPV types 16, 18, 31, 33, 35, 39, 45, 51, 52, 56, 58, 59, 66 and 68 in the test sample.

In still another aspect, the present invention relates to a kit for detecting HPV types 16, 18, 31, 33, 35, 39, 45, 51, 52, 56, 58, 59, 66 and 68 in a test sample. The kit comprises:

(a) at least one forward primer having a sequence selected from the group consisting of: SEQ ID NO:1, SEQ ID NO:2, SEQ ID NO:3, complements thereof and any combinations thereof;

(b) at least one reverse primer having a sequence selected from the group consisting of: SEQ ID NO:4, SEQ ID NO:5, complements thereof and any combinations thereof; and (c) amplification reagents.

The above described kit can also further comprise at least one probe, wherein at least one probe is selected from the group consisting of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof.

The above described kit further comprises probes having the sequence of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof.

In yet another aspect, the present invention relates to a primer and probe kit for detecting HPV types 16, 18, 31, 33, 35, 39, 45, 51, 52, 56, 58, 59, 66 and 68 in a test sample. The kit comprises:

(a) three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof;

(b) fourteen probes having a sequence of: SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof; and (c) amplification reagents.

The above kit can further comprise a forward primer having a sequence of SEQ ID NO:6 or a complement thereof and a reverse primer having a sequence of SEQ ID NO:7 or a complement thereof and a probe having a sequence of SEQ ID NO:22 or a complement thereof for detecting human beta globin in the test sample.

In still yet another aspect, the present invention relates to a primer and probe kit for detecting human beta globin in a test sample. The kit comprises:

(a) a forward primer having a sequence of SEQ ID NO: 6 or a complement thereof and a reverse primer having a sequence of SEQ ID NO:7 or a complement thereof;

(b) a probe having a sequence of SEQ ID NO:22 or a complement thereof; and (c) amplification reagents.

The above kit can further comprise:

(d) three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof; and (e) fourteen probes having a sequence of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof, for detecting HPV types 16, 18, 31, 33, 35, 39, 45, 51, 52, 56, 58, 59, 66 and 68 in the test sample.

DETAILED DESCRIPTION

Figure 1:
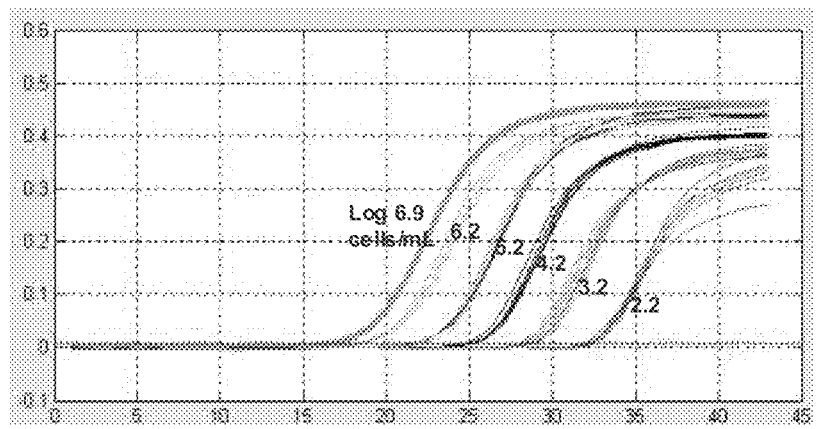
FIG. 1 shows the correlation between beta globin signal and the amount of cells spiked from a cultured HPV positive cell line and the distribution of the beta globin cycle number for a population of 1206 patient cervical specimens as described in Example 4.

The present invention relates to primers, probes, primer sets and primer and probe sets that can be used to amplify and/or detect HPV types 16, 18, 31, 33, 35, 39, 45, 51, 52, 56, 58, 59, 66 and 68 in a test sample. The present invention also relates to methods of detecting HPV types 16, 18, 31, 33, 35, 39, 45, 51, 52, 56, 58, 59, 66 and 68 in test samples using the primer and probe sets described herein. Additionally, the present invention also relates to primers, probes and primer and probe sets that can be used to amplify and/or detect human beta globin sequences in a test sample. The primers and probe used to amplify and/or detect human beta globin in a test sample can be used to generate internal control amplicons in an HPV assay. Additionally, the present invention also relates to methods of detecting human beta globin sequences in test samples using the primer and probe sets described herein. The present invention also relates to kits for detecting HPV types 16, 18, 31, 33, 35, 39, 45, 51, 52, 56, 58, 59, 66 and 68 and/or human beta globin sequences in a test sample.

The primer and probe sets of the present invention achieve robust clinical sensitivity and specificity. Additionally, the primer and probe sets described herein do not exhibit any cross-reactivity between HPV types. Moreover, the primer and probe sets of the present invention are capable of detecting multiple HPV genotypes in a single reaction while at the same time differentiating the detection of certain genotypes from others (e.g., partial genotyping). Finally, the primer and probe sets of the present invention provide high throughput and efficient workflow.

A. Definitions

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Amplicon

As used herein, the term "amplicon" refers to a product of a natural or artificial amplification reaction. An example of an amplicon is a DNA or RNA product (usually a segment of a gene, DNA or RNA) produced as a result of PCR, real-time PCR, RT-PCR, competitive RT-PCR, ligase chain reaction (LCR), gap LCR, strand displacement amplification (SDA), nucleic acid sequence based amplification (NASBA), transcription-mediated amplification (TMA) or the like.

b) Amplification, Amplification Method or Amplification Reaction

As used herein, the phrases "amplification", "amplification method" or "amplification reaction" as referred to interchangeably herein, refer to a method or process that increases the representation of a population of specific nucleic acid (all types of DNA or RNA) sequences (such as a target sequence or a target nucleic acid) in a test sample. Example of amplification methods that can be used in the present invention include, but are not limited to, PCR, real-time PCR, RT-PCR, competitive RT-PCR, LCR, gap LCR, SDA, NASBA, TMA and the like, all of which are known to one skilled in the art.

c) Amplification Conditions

As used herein, the phrase "amplification conditions" refers to conditions that promote annealing and/or extension of primer sequences. Such conditions are well-known in the art and depend on the amplification method selected. For example, PCR amplification conditions generally comprise thermal cycling, e.g., cycling of the reaction mixture between two or more temperatures. In isothermal amplification reactions, amplification occurs without thermal cycling although an initial temperature increase may be required to initiate the reaction. Amplification conditions encompass all reaction conditions including, but not limited to, temperature and temperature cycling, buffer, salt, ionic strength, pH, and the like.

d) Amplification Reagents

As used herein, the phrase "amplification reagents" refers to reagents used in amplification reactions and may include, but are not limited to, buffers, reagents, enzymes having reverse transcriptase and/or polymerase activity or exonuclease activity; enzyme cofactors such as magnesium or manganese; salts; and deoxynucleotide triphosphates (dNTPs) such as deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP). Amplification reagents may readily be selected by one skilled in the art depending on the amplification method employed.

e) Directly Detectable and Indirectly Detectable

As used herein, the phrase, "directly detectable", when used in reference to a detectable label or detectable moiety, means that the detectable label or detectable moiety does not require further reaction or manipulation to be detectable. For example, a fluorescent moiety is directly detectable by fluorescence spectroscopy methods. In contrast, the phrase "indirectly detectable", when used herein in reference to a detectable label or detectable moiety, means that the detectable label or detectable moiety becomes detectable after further reaction or manipulation. For example, a hapten becomes detectable after reaction with an appropriate antibody attached to a reporter, such as a fluorescent dye.

f) Fluorophore, Fluorescent Moiety, Fluorescent Label or Fluorescent Dye

The terms, "fluorophore", "fluorescent moiety", "fluorescent label" and "fluorescent dye" are used interchangeably herein and refer to a molecule that absorbs a quantum of electromagnetic radiation at one wavelength, and emits one or more photons at a different, typically longer, wavelength in response thereto. Numerous fluorescent dyes of a wide variety of structures and characteristics are suitable for use in the practice of the present invention. Methods and materials are known for fluorescently labeling nucleic acid molecules (See, R. P. Haugland, "*Molecular Probes: Handbook of Fluorescent Probes and Research Chemicals 1992-1994*", 5th Ed., 1994, Molecular Probes, Inc.). Preferably, a fluorescent label or moiety absorbs and emits light with high efficiency (e.g., has a high molar absorption coefficient at the excitation wavelength used, and a high fluorescence quantum yield), and is photostable (e.g., does not undergo significant degradation upon light excitation within the time necessary to perform the analysis). Rather than being directly detectable themselves, some fluorescent dyes transfer energy to another fluorescent dye in a process called fluorescent resonance energy transfer (FRET), and the second dye produces the detected signal. Such FRET fluorescent dye pairs are also encompassed by the term "fluorescent moiety". The use of physically linked fluorescent reporter/quencher moiety is also within the scope of the present invention. In these aspects, when the fluorescent reporter and quencher moiety are held in close proximity, such as at the ends of a probe, the quencher moiety prevents detection of a fluorescent signal from the reporter moiety. When the two moieties are physically separated such as after cleavage by a DNA polymerase, the fluorescent signal from the reporter moiety becomes detectable.

g) Hybridization

As used herein, the term "hybridization" refers to the formation of complexes between nucleic acid sequences which are sufficiently complementary to form complexes via Watson-Crick base pairing or non-canonical base pairing. For example, when a primer "hybridizes" with a target sequence (template), such complexes (or hybrids) are sufficiently stable to serve the priming function required by, e.g., the DNA polymerase, to initiate DNA synthesis. It will be appreciated by one skilled in the art that hybridizing sequences need not have perfect complementarity to provide stable hybrids. In many situations, stable hybrids will form where fewer than about 10% of the bases are mismatches. Accordingly, as used herein, the term "complementary" refers to an oligonucleotide that forms a stable duplex with its complement under assay conditions, generally where there is about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater homology. Those skilled in the art understand how to estimate and adjust the stringency of hybridization conditions such that sequences having at least a desired level of complementarity will stably hybridize, while those having lower complementarity will not. Examples of hybridization conditions and parameters can be found, for example in, Sambrook et al., "*Molecular Cloning: A Laboratory Manual*", 1989, Second Edition, Cold Spring Harbor Press: Plainview, N.Y.; F. M. Ausubel, "*Current Protocols in Molecular Biology*", 1994, John Wiley & Sons: Secaucus, N.J.

h) Labeled or Labeled with a Detectable Label

As used herein, the terms "labeled" and "labeled with a detectable label (or agent or moiety)" are used interchangeably herein and specify that an entity (e.g., a primer or a probe) can be visualized, for example following binding to another entity (e.g., an amplification product or amplicon). Preferably, the detectable label is selected such that it generates a signal which can be measured and whose intensity is related to (e.g., proportional to) the amount of bound entity. A wide variety of systems for labelling and/or detecting nucleic acid molecules, such as primer and probes, are well-known in the art. Labeled nucleic acids can be prepared by incorporation of, or conjugation to, a label that is directly or indirectly detectable by spectroscopic, photochemical, biochemical, immunochemical, electrical, optical, chemical or other means. Suitable detectable agents include, but are not limited to, radionuclides, fluorophores, chemiluminescent agents, microparticles, enzymes, colorimetric labels, magnetic labels, haptens, Molecular Beacons, aptamer beacons and the like.

i) Primer

The term "primer" refers to an oligonucleotide which is capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). The primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present invention have a length of about 15 to 50 nucleotides in length, preferably from about 20 to about 40 nucleotides in length, most preferably, from about 22 to 30 nucleotides in length. The primers of the present invention can contain additional nucleotides in addition to those described in more detail herein. For example, primers used in SDA can include a restriction endonuclease recognition site 5' to the target binding sequence (See, U.S. Pat. Nos. 5,270,184 and 5,455,166), NASBA, and TMA primers can include an RNA polymerase promoter linked to the target binding sequence of the primer. Methods for linking such specialized sequences to a target binding sequence for use in a selected amplification reaction are well known to those skilled in the art. Additionally, in certain instances, a primer can be labeled with a detectable label.

The phrase "forward primer" refers to a primer that hybridizes (or anneals) with the target sequence (e.g., template strand). The phrase "reverse primer" refers to a primer that hybridizes (or anneals) to the complementary strand of the target sequence. The forward primer hybridizes with the target sequence 5' with respect to the reverse primer.

j) Primer Set

As used herein, the term "primer set" refers to two or more primers which together are capable of priming the amplification of a target sequence or target nucleic acid of interest (e.g., a target sequence within the HPV). In certain embodiments, the term "primer set" refers to a pair of primers including a 5' (upstream) primer (or forward primer) that hybridizes with the 5'-end of the target sequence or target nucleic acid to be amplified and a 3' (downstream) primer (or reverse primer) that hybridizes with the complement of the target sequence or target nucleic acid to be amplified. Such primer sets or primer pairs are particularly useful in PCR amplification reactions.

k) Probe

As used herein, the term "probe" refers to an oligonucleotide capable of selectively hybridizing to at least a portion of a target sequence under appropriate amplification conditions (e.g., a portion of a target sequence that has been amplified). In general, a probe sequence is identified as being either "complementary" (i.e., complementary to the coding or sense strand (+)), or "reverse complementary" (i.e., complementary to the anti-sense strand (−)). The probes of the present invention have a length of about 10-50 nucleotides, preferably about 12-35 nucleotides and most preferably from 14-25 nucleotides. In certain instances, a probe can be labeled with a detectable label.

l) Primer and Probe Set

As used herein, the phrase "primer and probe set" refers to a combination comprising two or more primers which together are capable of priming the amplification of a target sequence or target nucleic acid and least one probe which can detect the target sequence or target nucleic acid. The probe generally hybridizes to a strand of an amplification product (or amplicon) to form an amplification product/probe hybrid, which can be detected using routine techniques known to those skilled in the art.

m) Target Sequence or Target Nucleic Acid

The phrases "target sequence" and "target nucleic acid" are used interchangeably herein and refer to that which the presence or absence of which is desired to be detected. In the context of the present invention, a target sequence preferably includes a nucleic acid sequence to which one or more primers will complex. The target sequence can also include a probe-hybridizing region with which a probe will form a stable hybrid under appropriate amplification conditions. As will be recognized by one of ordinary skill in the art, a target sequence may be single-stranded or double-stranded. In the context of the present invention, target sequences of interest are located within the L1 region of HPV or the open reading frame of the human beta globin gene.

n) Test Sample

As used herein, the term "test sample" generally refers to a biological material being tested for and/or suspected of containing an analyte of interest, such as HPV, particularly, HPV types 16, 18, 31, 33, 35, 39, 45, 51, 52, 56, 58, 59, 66 and 68, human beta globin sequences or combinations thereof. The test sample may be derived from any biological source, such as, a cervical, vaginal or anal swab or brush, or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen and so forth. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

B. Primers, Probes and Primer and Probe Sets

In one embodiment, the present invention relates to one or more primers for amplifying human papillomavirus (HPV) types 16, 18, 31, 33, 35, 39, 45, 51, 52, 56, 58, 59, 66 and 68 in a test sample. The one or more primers can include a primer having a sequence comprising or consisting of any of the sequences shown below in Table A, a complement of any of the sequences shown below in Table A and any combinations of the sequences shown below in Table A and/or their complements.

TABLE A

| SEQ ID NO: | SEQUENCE | Type of Primer |
|---|---|---|
| 1 | tatttgttac tgtggtagat actac | Forward Primer |
| 2 | caattgtttg ttactgttgt ggatactac | Forward Primer |
| 3 | tttttattac ctgtgttgat actac | Forward Primer |
| 4 | gaaaaataaa ctgtaaatca tattcctc | Reverse Primer |
| 5 | gaaaaataaa ttgcaattca tactcttc | Reverse Primer |

In one aspect, the present invention relates to a primer set for amplifying HPV types 16, 18, 31, 33, 35, 39, 45, 51, 52, 56, 58, 59, 66 and 68 in a test sample containing one or more of the primers described in Table A. Specifically, the primer set can comprise the following:

(a) at least one forward primer having a sequence selected from the group consisting of: SEQ ID NO:1, SEQ ID NO:2, SEQ ID NO:3, complements thereof (e.g., one or more complements of SEQ ID NO:1, SEQ ID NO:2 or SEQ ID NO:3) and any combinations thereof; and (b) at least one reverse primer having a sequence selected from the group consisting of: SEQ ID NO:4, SEQ ID NO:5, complements thereof (e.g., one or more complements of SEQ ID NO:4 or SEQ ID NO:5) and any combinations thereof.

In another embodiment, the present invention relates to one or more probes for detecting HPV types 16, 18, 31, 33, 35, 39, 45, 51, 52, 56, 58, 59, 66 and 68 in a test sample. The one or more probes can include a probe having a sequence comprising or consisting of any of the sequences shown below in Table B, a complement of any of the sequences shown below in Table B and any combinations of the sequences shown below in Table B and/or their complements. For example, the one or more probes can be only a single probe listed below in Table B or only a single complement of one of the probes listed below in Table B (such as for example, (a) SEQ ID NO:8; (b) the complement of SEQ ID NO:10; (c) SEQ ID NO:12; or (d) SEQ ID NO:21), all of the probes listed below in Table B (SEQ ID NOS: 8-21), complements of all the probes listed below in Table B (complements of SEQ ID NOS:8-21) or any combinations of the probes listed below in Table B and/or the complements of the probes listed below in Table B (such as, for example, (a) SEQ ID NO:10 and SEQ ID NO:16; (b) SEQ ID NO:8, the complement of SEQ ID NO:9, SEQ ID NO:10, SEQ ID NO:15 and SEQ ID NO:21; (c) the complement of SEQ ID NO:8, the complement of SEQ ID NO:9 and SEQ ID NO:16; (d) SEQ ID NO:11, SEQ ID NO:17, the complement of SEQ ID NO:18 and the complement of SEQ ID NO:20; (e) SEQ ID NO:8, SEQ ID NO:9, the complement of SEQ ID NO:12, the complement of SEQ ID NO:14 and SEQ ID NO:20); or (f) SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:18, SEQ ID NO:19 and SEQ ID NO:20).

TABLE B

| SEQ ID NO: | SEQUENCE (5' to 3') | HPV Type Specificity |
|---|---|---|
| 8 | atgtgctgcc atatctactt ca | HPV type 16 |
| 9 | cacagtctcc tgtacctggg ca | HPV type 18 |
| 10 | taaaagtagt aattttaaag ag | HPV type 31 |
| 11 | atgcacacaa gtaactagt | HPV type 33 |
| 12 | ctgtgtgttc tgctgtgtc | HPV type 35 |
| 13 | tccatacctt ctac | HPV type 39 |
| 14 | cctactaagt ttaagcagta ta | HPV type 45 |
| 15 | ttagcactgc cactgctgc | HPV type 51 |
| 16 | aaaaaggaaa gcac | HPV type 52 |
| 17 | ctacagaaca gttaagtaa | HPV type 56 |
| 18 | atgcactgaa gtaa | HPV type 58 |
| 19 | attcctaatg tatacacacc tacc | HPV type 59 |
| 20 | caatcaatac cttcgccatg tg | HPV type 66 |
| 21 | ctttgtctac tactactga | HPV type 68 |

In another embodiment, the present invention relates to a primer and probe set for detecting HPV types 16, 18, 31, 33, 35, 39, 45, 51, 52, 56, 58, 59, 66 and 68 in a test sample containing one or more of the primers described above in Table A and one or more of the probes described above in Table B. For example, the primer and probe set can comprise the following:

(a) at least one forward primer having a sequence of: SEQ ID NO:1, SEQ ID NO:2 and SEQ ID NO:3 or complements thereof and at least one reverse primer having a sequence of: SEQ ID NO:4 and SEQ ID NO:5 or complements thereof; and (b) at least one probe having a sequence of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or a complement thereof.

Preferably, the primer and probe set comprises:

(a) three forward primers having a sequence of: SEQ ID NO:1, SEQ ID NO:2 and SEQ ID NO:3 or complements thereof and two reverse primers having a sequence of: SEQ ID NO:4 and SEQ ID NO:5 or complements thereof; and (b) fourteen probes having a sequence of: SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or complements thereof.

In yet another embodiment, the present invention relates to a primer for amplifying a human beta globin sequence in a test sample. The one or more primers can be a primer having a sequence comprising or consisting of any of the sequences shown below in Table C, a complement of any of the sequences shown below in Table C and any combinations of the sequences shown below in Table C and/or their complements.

TABLE C

| SEQ ID NO: | SEQUENCE | Type of Primer |
| --- | --- | --- |
| 6 | ggcaggttgg tatcaaggtt ac | Forward Primer |
| 7 | cctaagggtg ggaaaataga cc | Reverse Primer |

In yet another embodiment, the present invention relates to a probe for detecting a human beta globin sequence in a test sample. The probe has a sequence comprising or consisting of a sequence of: actgggcatg tggagacaga (SEQ ID NO:22) or its complement thereof.

In yet another embodiment, the present invention relates to a primer set for amplifying endogenous human beta globin in a test sample comprising at least two primers selected from the group consisting of: SEQ ID NO:6, SEQ ID NO:7, a complement of SEQ ID NO:6 and a complement of SEQ ID NO:7. Preferably, the primer set comprises SEQ ID NO:6 and SEQ ID NO:7.

In yet another embodiment, the present invention relates to a primer and probe set for detecting endogenous human beta globin in a test sample containing one or more of the primers described above in Table C or a complement thereof and a probe having the sequence of SEQ ID NO:22 or a complement thereof. For example, the primer and probe set can comprise:

(a) at least one primer having a sequence of SEQ ID NO: 6, SEQ ID NO:7, a complement of SEQ ID NO:6 or a complement of SEQ ID NO:7; and
(b) a probe having a sequence of SEQ ID NO:22 or a complement thereof.

Preferably, the primer and probe set comprises:

(a) a forward primer having a sequence of SEQ ID NO: 6 or a complement thereof and a reverse primer having a sequence of SEQ ID NO:7 or a complement thereof; and
(b) a probe having a sequence of SEQ ID NO:22 or a complement thereof.

The primers and probe described above for amplifying and detecting human beta globin in a test sample can be used to generate internal control (IC) amplicons in an HPV assay. The detection of human beta globin in a HPV assay serves as a sample validity control for cell adequacy, sample extraction and amplification efficacy. More specifically, this internal control serves to confirm that each test sample has sufficient cell input for accurate HPV detection and has been processed correctly, and further indicates whether inhibitors of amplification are present.

One or more oligonucleotide analogues can be prepared based on the primers and probes of the present invention. Such analogues may contain alternative structures such as peptide nucleic acids or "PNAs" (e.g, molecules with a peptide-like backbone instead of the phosphate sugar backbone of naturally occurring nucleic acids) and the like. These alternative structures, are also encompassed by the present invention. Similarly, it is understood that the primers and probes of the present invention may contain deletions, additions and/or substitutions of nucleic acid bases, to the extent that such alterations do not negatively affect the properties of these sequences. In particular, the alterations should not result in a significant decrease of the hybridizing properties of the primers and probes described herein.

The primers and probes of the present invention may be prepared by any of a variety of methods known in the art (See, for example, Sambrook et al., "*Molecular Cloning. A Laboratory Manual*", 1989, 2. Supp. Ed., Cold Spring Harbour Laboratory Press: New York, N.Y.; "*PCR Protocols. A Guide to Methods and Applications*", 1990, M. A. Innis (Ed.), Academic Press: New York, N.Y.; P. Tijssen "*Hybridization with Nucleic Acid Probes—Laboratory Techniques in Biochemistry and Molecular Biology* (Parts I and II)", 1993, Elsevier Science; "*PCR Strategies*", 1995, M. A. Innis (Ed.), Academic Press: New York, N.Y.; and "*Short Protocols in Molecular Biology*", 2002, F. M. Ausubel (Ed.), 5. Supp. Ed., John Wiley & Sons: Secaucus, N.J.). For example, primers and probes described herein may be prepared by chemical synthesis and polymerization based on a template as described, for example, in Narang et al., *Meth. Enzymol.*, 1979, 68: 90-98; Brown et al., *Meth. Enzymol.*, 1979, 68: 109-151 and Belousov et al., *Nucleic Acids Res.*, 1997, 25: 3440-3444).

For example, primers and probes may be prepared using an automated, solid-phase procedure based on the phosphoramidite approach. In such a method, each nucleotide is individually added to the 5'-end of a growing oligonucleotide chain, which is attached at the 3'-end to a solid support. The added nucleotides are in the form of trivalent 3'-phosphoramidites that are protected by a dimethoxytriyl (or DMT) group at the 5' position. After base-induced phosphoramidite coupling, mild oxidation to give a pentavalent phosphotriester intermediate and DMT removal provides a new site for oligonucleotide elongation. The primer or probe is then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, the primers and probes of the present invention can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), BioSearch Technologies, Inc. (Novato, Calif.), and many others.

Purification of the primers and probes of the present invention, where necessary or desired, may be carried out by any of a variety of methods well-known in the art. Purification of primers and probes can be performed either by native acrylamide gel electrophoresis, by anion-exchange HPLC as described, for example, by Pearson et al., *J. Chrom.*, 1983, 255: 137-149 or by reverse phase HPLC (See, McFarland et al., *Nucleic Acids Res.*, 1979, 7: 1067-1080).

The sequence of the primers and probes can be verified using any suitable sequencing method known in the art, including, but not limited to, chemical degradation (See, Maxam et al., *Methods of Enzymology*, 1980, 65: 499-560), matrix-assisted laser desorption ionization time-of-flight (MALDI-TOF) mass spectrometry (See, Pieles et al., *Nucleic Acids Res.*, 1993, 21: 3191-3196), mass spectrometry following a combination of alkaline phosphatase and exonuclease digestions (Wu et al. *Anal. Biochem.*, 2001, 290: 347-352), and the like.

As already mentioned above, modified primers and probes may be prepared using any of several means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc), or charged linkages (e.g., phosphorothioates, phosphorodithioates, etc). Primers and probes may contain one or more additional covalently linked moieties, such as, for example, proteins (e.g., nucleases, toxins, antibodies, signal peptides, poly-L-lysine, etc), intercalators (e.g., acridine, psoralen, etc), chelators (e.g., to chelate metals, radioactive metals, oxidative metals, etc), and alkylators. Primers and probes may also be derivatized by formation of a methyl or ethyl phosphotriester or an alkyl phosphoramidate linkage. Furthermore, the primers, probes or primers and probes of the present invention may also be modified with a detectable label.

As alluded to above, in certain embodiments of the present invention, the primers, the probes or both the primers and probes can be labeled with a detectable label or moiety before being used in amplification/detection methods. Preferably, for use in the methods described herein, one or more probes is labeled with a detectable label or moiety. The role of a detectable label is to allow visualization and detection of amplified target sequences (e.g., amplicons). Preferably, the detectable label is selected such that it generates a signal which can be measured and whose intensity is related (e.g., proportional) to the amount of amplification product in the test sample being analyzed.

The association between one or more probes and detectable label can be covalent or non-covalent. Labeled probes can be prepared by incorporation of, or conjugation to, a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules (See, for example, Mansfield et al., *Mol. Cell. Probes,* 1995, 9: 145-156).

Methods for labeling oligonucleotides, such as probes, are well-known to those skilled in the art. Reviews of labeling protocols and label detection techniques can be found, for example in, L. J. Kricka, *Ann. Clin. Biochem.,* 2002, 39: 114-129; van Gijlswijk et al., *Expert Rev. Mol. Diagn.,* 2001, 1: 81-91; and Joos et al., *J. Biotechnol.,* 1994, 35: 135-153. Standard nucleic acid labeling methods include: incorporation of radioactive agents, direct attachments of fluorescent dyes (See, Smith et al., *Nucl. Acids Res.,* 1985, 13: 2399-2412) or of enzymes (See, Connolly et al., *Nucl. Acids. Res.,* 1985, 13: 4485-4502); chemical modifications of nucleic acid molecules making them detectable immunochemically or by other affinity reactions (See, Broker et al., *Nucl. Acids Res.,* 1978, 5: 363-384; Bayer et al., *Methods of Biochem. Analysis,* 1980, 26: 1-45; Langer et al., *Proc. Natl. Acad. Sci. USA,* 1981, 78: 6633-6637; Richardson et al., *Nucl. Acids Res.,* 1983, 11: 6167-6184; Brigati et al., *Virol.,* 1983, 126: 32-50; Tchen et al., *Proc. Natl. Acad. Sci. USA,* 1984, 81: 3466-3470; Landegent et al., *Exp. Cell Res.,* 1984, 15: 61-72; and A. H. Hopman et al., *Exp. Cell Res.,* 1987, 169: 357-368); and enzyme-mediated labeling methods, such as random priming, nick translation, PCR and tailing with terminal transferase (For a review on enzymatic labeling, see, for example, Temsamani et al., *Mol. Biotechnol.,* 1996, 5: 223-232).

Any of a wide variety of detectable labels can be used in the present invention. Suitable detectable labels include, but are not limited to, various ligands, radionuclides (e.g., $^{32}P$, $^{35}S$, $^{3}H$, $^{14}C$, $^{125}I$, $^{131}I$, and the like); fluorescent dyes; chemiluminescent agents (e.g., acridinium esters, stabilized dioxetanes, and the like); spectrally resolvable inorganic fluorescent semiconductor nanocrystals (e.g., quantum dots), metal nanoparticles (e.g., gold, silver, copper and platinum) or nanoclusters; enzymes (e.g., horseradish peroxidase, beta-galactosidase, luciferase, alkaline phosphatase); colorimetric labels (e.g., dyes, colloidal gold, and the like); magnetic labels (e.g., sold under DYNABEADS); and biotin, dioxigenin or other haptens and proteins for antisera or monoclonal antibodies are available.

In certain embodiments, the inventive detection probes are fluorescently labeled. Numerous known fluorescent labeling moieties of a wide variety of chemical structures and physical characteristics are suitable for use in the practice of this invention. Suitable fluorescent dyes include, but are not limited to, fluorescent dyes sold under QUASAR (available from Biosearch Technologies, Novato, Calif.), fluorescein and fluorescein dyes (e.g., fluorescein isothiocyanine or FITC, naphthofluorescein, 4',5'-dichloro-2',7'-dimethoxy-fluorescein, 6-carboxyfluoresceins (e.g., sold under FAM), fluorescent dyes sold under VIC, fluorescent dyes sold under NED, carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), fluorescent dyes sold under OREGON GREEN, OREGON GREEN 488, OREGON GREEN 500, OREGON GREEN 514, TEXAS RED, TEXAS RED-X, SPECTRUM RED, and SPECTRUM GREEN, cyanine dyes (e.g., sold under CY-3, CY-5, CY-3.5, and CY-5.5), fluorescent dyes sold under ALEXA FLUOR, ALEXA FLUOR 350, ALEXA FLUOR 488, ALEXA FLUOR 532, ALEXA FLUOR 546 ALEXA FLUOR 568, ALEXA FLUOR 594, ALEXA FLUOR 633, ALEXA FLOUR 660, and ALEXA FLUOR 680, fluorescent dyes sold under BODIPY, BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, and BODIPY 650/665, fluorescent dyes sold under IRDYES, IRD40, IRD 700, and IRD 800, and the like. Examples of other suitable fluorescent dyes that can be used and methods for linking or incorporating fluorescent dyes to oligonucleotides, such as probes, can be found in R P Haugland, "*The Handbook of Fluorescent Probes and Research Chemicals*", Publisher, Molecular Probes, Inc., Eugene, Oreg. (June 1992)). Fluorescent dyes as well as labeling kits are commercially available from, for example, Amersham Biosciences, Inc. (Piscataway, N.J.), Molecular Probes Inc. (Eugene, Oreg.), and New England Biolabs Inc. (Beverly, Mass.).

Rather than being directly detectable themselves, some fluorescent groups (donors) transfer energy to another fluorescent group (acceptor) in a process of fluorescent resonance energy transfer (FRET), and the second group produces the detectable fluorescent signal. In these embodiments, the probe may, for example, become detectable when hybridized to an amplified target sequence. Examples of FRET acceptor/donor pairs suitable for use in the present invention include, but are not limited to, fluorescein/tetramethylrhodamine, IAEDANS/FITC, IAEDANS/5-(iodoacetomido)fluorescein, B-phycoerythrin/Cy-5, and EDANS/Dabcyl.

The use of physically linked fluorescent reporter/quencher molecule pairs is also within the scope of the present invention. The use of such systems in quantitative PCR assays (e.g., sold under TAQMAN: as described, for example, in U.S. Pat. Nos. 5,210,015; 5,804,375; 5,487,792 and 6,214,979) or as Molecular Beacons (as described, for example in, Tyagi et al., *Nature Biotechnol.,* 1996, 14: 303-308; Tyagi et al., *Nature Biotechnol.,* 1998, 16: 49-53; Kostrikis et al., *Science,* 1998, 279:1228-1229; Sokol et al., *Proc. Natl. Acad. Sci. USA,* 1998, 95: 11538-11543; Marras et al., *Genet. Anal.,* 1999, 14:

151-156; and U.S. Pat. Nos. 5,846,726, 5,925,517, 6,277,581 and 6,235,504) is well-known to those skilled in the art. With the quantitative PCR assay format (e.g., sold under TAQ-MAN), products of the amplification reaction can be detected as they are formed in a "real-time" manner. As a result, amplification product/probe hybrids are formed and detected while the reaction mixture is under amplification conditions.

In some embodiments of the present invention, the PCR detection probes are probes that are labeled at the 5'-end with a fluorescent moiety and at the 3'-end with a quencher moiety. Suitable fluorophores and quenchers for use with such probes are disclosed in U.S. Pat. Nos. 5,210,015; 5,804,375; 5,487,792; and 6,214,979; and WO 01/86001, each of which are herein incorporated by reference. Examples of quenchers include, but are not limited to, DABCYL (e.g., 4-(4'-dimethylaminophenylazo)-benzoic acid)succinimidyl ester, diarylrhodamine carboxylic acid, succinimidyl ester (or a quencher sold under QSY-7), and 4',5'-dinitrofluorescein carboxylic acid, succinimidyl ester (or a quencher sold under QSY-33) (all of which are available from Molecular Probes (which is part of Invitrogen, Carlsbad, Calif.)), a quencher sold under QUENCHER1 (available from Epoch Biosciences, Bothell, Wash.), or a quencher sold under BLACK HOLE QUENCHERS, BHQ-1, BHQ-2, and BHQ-3 (available from BioSearch Technologies, Inc., Novato, Calif.). In certain embodiments, the PCR detection probes are probes that are labeled at the 5' end with a fluorescent label sold under FAM and at the 3' end with a quencher sold under BLACK HOLE QUENCHER or BLACK HOLE QUENCHER PLUS (both commercially available from Biosearch Technologies, Novato, Calif.).

A "tail" of normal or modified nucleotides can also be added to probes for detectability purposes. A second hybridization with nucleic acid complementary to the tail and containing one or more detectable labels (such as, for example, fluorophores, enzymes or bases that have been radioactively labeled) allows visualization of the amplicon/probe hybrids.

The selection of a particular labeling technique will depend on the situation and will be governed by several factors, such as the ease and cost of the labeling method, spectral spacing between different detectable labels used, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

C. Amplification Methods

The use of primers or primer sets of the present invention to amplify HPV types 16, 18, 31, 33, 35, 39, 45, 51, 52, 56, 58, 59, 66 and 68 target sequences and human beta globin target sequences in test samples is not limited to any particular nucleic acid amplification technique or any particular modification thereof. In fact, the primers and primer sets of the present invention can be employed in any of a variety of nucleic acid amplification methods that are known in the art (See, for example, Kimmel et al., *Methods Enzymol.*, 1987, 152: 307-316; Sambrook et al., "*Molecular Cloning. A Laboratory Manual*", 1989, 2. Supp. Ed., Cold Spring Harbour Laboratory Press: New York, N.Y.; "*Short Protocols in Molecular Biology*", F. M. Ausubel (Ed.), 2002, 5. Supp. Ed., John Wiley & Sons: Secaucus, N.J.).

Such nucleic acid amplification methods include, but are not limited to, the Polymerase Chain Reaction (PCR). PCR is described in a number of references, such as, but not limited to, "*PCR Protocols: A Guide to Methods and Applications*", M. A. Innis (Ed.), 1990, Academic Press: New York; "*PCR Strategies*", M. A. Innis (Ed.), 1995, Academic Press: New York; "*Polymerase chain reaction: basic principles and automation in PCR. A Practical Approach*", McPherson et al. (Eds.), 1991, IRL Press: Oxford; Saiki et al., *Nature*, 1986, 324: 163; and U.S. Pat. Nos. 4,683,195, 4,683,202 and 4,889,818, each of which is incorporated herein by reference in its entirety. Variations of PCR including, quantitative PCR-based assays (e.g., sold under TAQMAN; See, Holland et al., *Proc. Natl. Acad. Sci.*, 1991, 88: 7276-7280), and reverse transcriptase polymerase chain reaction (or RT-PCR, described in, for example, U.S. Pat. Nos. 5,322,770 and 5,310,652, each of which is incorporated by reference) are also included.

Generally, in PCR, a pair of primers is added to a test sample obtained from a subject (and thus contacted with the test sample) in excess to hybridize to the complementary strands of the target nucleic acid. The primers are each extended by a DNA polymerase using the target sequence as a template. The extension products become targets themselves after dissociation (denaturation) from the original target strand. New primers are then hybridized and extended by the polymerase, and the cycle is repeated to exponentially increase the number of copies of amplicons. Examples of DNA polymerases capable of producing primer extension products in PCR reactions include, but are not limited to, *E. coli* DNA polymerase I, Klenow fragment of DNA polymerase I, T4 DNA polymerase, thermostable DNA polymerases isolated from *Thermus aquaticus* (Taq), available from a variety of sources (e.g., Perkin Elmer, Waltham, Mass.), *Thermus thermophilus* (USB Corporation, Cleveland, Ohio), *Bacillus stereothermophilus* (Bio-Rad Laboratories, Hercules, Calif.), a DNA polymerase sold under AMPLITAQ GOLD (Applied Biosystems, Foster City, Calif.), recombinant *Thermus thermophilus*(rTth) DNA polymerase (Applied Biosystems, Foster City, Calif.) or *Thermococcus litoralis*e.g., the DNA polymerase sold under VENT, New England Biolabs, Ipswich, Mass.). RNA target sequences may be amplified by reverse transcribing (RT) the mRNA into cDNA, and then performing PCR (RT-PCR), as described above. Alternatively, a single enzyme may be used for both steps as described in U.S. Pat. No. 5,322,770, which is herein incorporated by reference.

In addition to the enzymatic thermal amplification methods described above, isothermal enzymatic amplification reactions can be employed to amplify HPV or beta globin target sequences using primers and primer sets of the present invention (Andras et al., *Mol. Biotechnol.*, 2001, 19: 29-44). These methods include, but are not limited to, Transcription-Mediated Amplification (TMA; TMA is described in Kwoh et al., *Proc. Natl. Acad. Sci. USA*, 1989, 86: 1173-1177; Giachetti et al., *J. Clin. Microbiol.*, 2002, 40: 2408-2419; and U.S. Pat. No. 5,399,491); Self-Sustained Sequence Replication (3SR; 3SR is described in Guatelli et al., *Proc. Natl. Acad. Sci. USA*, 1990, 87: 1874-1848; and Fahy et al., *PCR Methods and Applications*, 1991, 1: 25-33); Nucleic Acid Sequence Based Amplification (NASBA; NASBA is described in, Kievits et al., *J. Virol. Methods*, 1991, 35: 273-286; and U.S. Pat. No. 5,130,238) and Strand Displacement Amplification (SDA; SDA is described in Walker et al., *PNAS*, 1992, 89: 392-396; EP 0 500 224 A2).

Strand-displacement amplification combines the ability of a restriction endonuclease to nick the unmodified strand of its target DNA and the action of an exonuclease-deficient DNA polymerase to extend the 3' end at the nick and displace the downstream DNA strand at a fixed temperature (See, Walker et al., *Proc. Natl. Acad. Sci. USA*, 1992). Primers used in SDA include a restriction endonuclease recognition at site 5' to the target binding sequence (See, U.S. Pat. Nos. 5,270,184 and 5,344,166, each of which is incorporated herein by reference).

Nucleic Acid Sequence Based Amplification (NASBA) uses three enzymes (e.g., RNase H, avian myeloblastosis virus (AMV) reverse transcriptase and T7 RNA polymerase) working in concert at a low isothermal temperature, generally 41° C. (See, Compton, *Nature,* 1991, 350: 91-92; Chan et al., *Rev. Med. Microbiol.,* 1999, 10: 185-196). The product of a NASBA reaction is mainly single-stranded RNA.

The Self Sustaining Sequence Replication (3SR) reaction is a very efficient method for isothermal amplification of target DNA or RNA sequences. A 3SR system involves the collective activities of AMV reverse transcriptase, *E. coli* RNase H, and DNA-dependent RNA polymerase (e.g., T7 RNA polymerase).

Transcription-Mediated Amplification (TMA) uses an RNA polymerase to make RNA from a promoter engineered in the primer region, a reverse transcriptase to produce complementary DNA from the RNA templates and RNase H to remove the RNA from cDNA (See, Guatelli et al., *Proc. Natl. Acad. Sci. USA,* 1990).

NASBA, 3SR, and TMA primers require an RNA polymerase promoter linked to the target binding sequence of the primer. Promoters or promoter sequences for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are generated. Examples of useful promoters include those which are recognized by certain bacteriophage polymerases such as those from bacteriophage T3, T7 or SP6 or a promoter from *E. coli.*

D. Detection Methods

In certain embodiments of the present invention, the probes described herein are used to detect amplification products generated by the amplification reaction. The probes described herein can be employed using a variety of well-known homogeneous or heterogeneous methodologies.

Homogeneous detection methods include, but are not limited to, the use of FRET labels that are attached to the probes and that emit a signal in the presence of the target sequence, Molecular Beacons (See, Tyagi et al., *Nature Biotechnol.,* 1996, 14: 303-308; Tyagi et al., *Nature Biotechnol.,* 1998, 16: 49-53; Kostrikis et al., *Science,* 1998, 279: 1228-1229; Sokol et al., *Proc. Natl. Acad. Sci. USA,* 1998, 95: 11538-11543; Marras et al., *Genet. Anal.,* 1999, 14: 151-156; and U.S. Pat. Nos. 5,846,726, 5,925,517, 6,277,581 and 6,235,504), and the TaqMan® assays (See, U.S. Pat. Nos. 5,210,015; 5,804, 375; 5,487,792 and 6,214,979 and WO 01/86001). Using these detection techniques, products of the amplification reaction can be detected as they are formed, namely, in a real time manner. As a result, amplification product/probe hybrids are formed and detected while the reaction mixture is under amplification conditions.

In certain embodiments, the probes of the present invention are used in a quantitative PCR assay (e.g., sold under TAQ-MAN). In a quantitative PCR assay (e.g., sold under TAQ-MAN), analysis is performed in conjunction with thermal cycling by monitoring the generation of fluorescence signals. The assay system has the capability of generating quantitative data allowing the determination of target copy numbers. For example, standard curves can be generated using serial dilutions of previously quantified suspensions of one or more HPV types or human beta globin sequences, against which unknown samples can be compared. The quantitative PCR assay (e.g., sold under TAQMAN) is conveniently performed using, for example, a DNA polymerase, which has endogenous 5' nuclease activity (e.g., sold under AMPLITAQ GOLD), to digest a probe labeled with both a fluorescent reporter dye and a quencher moiety, as described above. Assay results are obtained by measuring changes in fluorescence that occur during the amplification cycle as the probe is digested, uncoupling the fluorescent and quencher moieties and causing an increase in the fluorescence signal that is proportional to the amplification of the target sequence.

Other examples of homogeneous detection methods include hybridization protection assays (HPA). In such assays, the probes are labeled with acridinium ester (AE), a highly chemiluminescent molecule (See, Weeks et al., *Clin. Chem.,* 1983, 29: 1474-1479; Berry et al., *Clin. Chem.,* 1988, 34: 2087-2090), using a non-nucleotide-based linker arm chemistry (See, U.S. Pat. Nos. 5,585,481 and 5,185,439). Chemiluminescence is triggered by AE hydrolysis with alkaline hydrogen peroxide, which yields an excited N-methyl acridone that subsequently deactivates with emission of a photon. In the absence of a target sequence, AE hydrolysis is rapid. However, the rate of AE hydrolysis is greatly reduced when the probe is bound to the target sequence. Thus, hybridized and un-hybridized AE-labeled probes can be detected directly in solution without the need for physical separation.

Heterogeneous detection systems are also well-known in the art and generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the invention. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any detection methods, such as those described herein.

E. Detecting Hpv and Human Beta Globin in Test Samples

In another embodiment, the present invention provides methods for: (a) detecting the presence of HPV types 16, 18, 31, 33, 35, 39, 45, 51, 52, 56, 58, 59, 66 and 68 in a test sample; (b) detecting human beta globin sequences in a test sample; and (c) detecting the presence of HPV types 16, 18, 31, 33, 35, 39, 45, 51, 52, 56, 58, 59, 66 and 68 and human beta globin sequences in a test sample.

Typically, methods of the invention first involve obtaining a test sample from a subject. A subject from which a test sample can be obtained is any mammal. Preferably, the mammal includes, but are not limited to, dogs, cats, rabbits, mice, rats, goats, sheep, cows, pigs, horses, non-human primates and humans. The test sample can be obtained from the subject using routine techniques known to those skilled in the art. Preferably, the test sample contains or is suspected of containing: (i) at least one of HPV types 16, 18, 31, 33, 35, 39, 45, 51, 52, 56, 58, 59, 66 and 68 and/or (ii) at least one human beta globin sequence.

After the test sample is obtained from a subject, the test sample is contacted with primers (and optionally one or more probes) from at least one of the primer sets or primer and probe sets disclosed herein to form a reaction mixture. The reaction mixture is then placed under amplification conditions. The primers hybridize to any HPV nucleic acid and any human beta globin nucleic acid in the test sample. The HPV or human beta globin nucleic acid present in the sample is amplified and at least one amplification product (namely, at least one target sequence) is generated.

At least one amplification product is detected by detecting the hybridization between at least one amplification product and at least one of the probes of the present invention (such as one or more probes from the primer and probe sets described herein). Specifically, detection of at least one amplification product with one or more of the probes having a sequence of SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or a complement thereof indicates the presence of at least one of HPV types 16, 18, 31, 33, 35, 39, 45, 51, 52, 56, 58, 59, 66 and 68 in the test sample. Detection of hybridization of the amplification product and the probe having a sequence of SEQ ID NO:22 or a complement thereof indicates the presence of a human beta globin sequence in the test sample. Preferably, the methods of the present invention involve detecting at least one of HPV types 16, 18, 31, 33, 35, 39, 45, 51, 52, 56, 58, 59, 66 and 68 and a human beta globin sequence (added as a control) in the test sample. Most preferably, the detection of least one HPV type and the human beta globin sequence are done simultaneously.

Additionally, the methods of the present invention may also be used to partially genotype (e.g, differentiate) the HPV type present and detected in a test sample. For example, each of the probes used in the methods described herein can be labeled with a different detectable label that emits a different color of light in order to facilitate the identification of different HPV types present in a test sample. Preferably, however, for use in the methods of the present invention, a probe having a sequence of SEQ ID NO:8 is labeled with a first detectable label that emits a unique color (e.g., red) and a probe having a sequence of SEQ ID NO:9 is labeled a second detectable label that is different from the first detectable label and that also emits a unique color (e.g., green). If one or more of the probes having the sequence of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21 or a complement thereof are also to be used in the method along with SEQ ID NOS: 8 and 9, each of these probes could be labeled with the same detectable label (namely, each would be labeled with a third detectable label emitting a third unique color (e.g., yellow)). Thus, employing different types of labels with the different HPV probes described herein (See, Table B) allows not only detecting the presence of HPV in a test sample but also specifically identifying the specific types present in the sample. The detection and/or differentiation of HPV types 16 and 18 (such as by using probes having a sequence of SEQ ID NO:8 and SEQ ID NO:9) in a test sample is useful and important because these two types of HPV cause at least 70% of the cervical cancers.

F. Kits

In another embodiment, the present invention provides kits comprising materials and reagents useful for the detection of HPV types 16, 18, 31, 33, 35, 39, 45, 51, 52, 56, 58, 59, 66and 68 and human beta globin sequences according to methods described herein. The kits can be used by diagnostic laboratories, experimental laboratories, or practitioners. In certain embodiments, the kits comprise at least one of the primer sets or primer and probe sets described in Section B herein and optionally, amplification reagents. Each kit preferably comprises amplification reagents for a specific amplification method. Thus, a kit adapted for use with NASBA preferably contains primers with a RNA polymerase promoter linked to the target binding sequence, while a kit adapted for use with SDA preferably contains primers including a restriction endonuclease recognition site 5' to the target binding sequence. Similarly, when the kit is adapted for use in a 5' nuclease assay, such as the quantitative PCR assay (e.g., sold under TAQMAN), the probes of the present invention can contain at least one fluorescent reporter moiety and at least one quencher moiety.

Suitable amplification reagents additionally include, for example, one or more of: buffers, reagents, enzymes having reverse transcriptase and/or polymerase activity or exonuclease activity, enzyme cofactors such as magnesium or manganese; salts; deoxynucleotide triphosphates (dNTPs) suitable for carrying out the amplification reaction. For example, a kit, adapted for use with NASBA, may contain suitable amounts of reverse transcriptase, RNase H and T7 RNA polymerase. In kits adapted for transcription amplification reactions, such as NASBA, buffers can be included that contain, for example, DMSO, which is known to enhance the amplification reaction.

Depending on the procedure, kits may further comprise one or more of: wash buffers, hybridization buffers, labeling buffers, detection means and other reagents. The buffers and/or reagents are preferably optimized for the particular amplification/detection technique for which the kit is intended. Protocols for using these buffers and reagents for performing different steps of the procedure may also be included in the kit.

Furthermore, kits may be provided with an internal control as a check on the amplification efficiency, to prevent occurrence of false negative test results due to failures in the amplification, to check on cell adequacy, sample extraction, etc. An optimal internal control sequence is selected in such a way that it will not compete with the target nucleic acid sequence in the amplification reaction. Preferably, the internal control comprises the beta globin primers (namely, at least one of SEQ ID NO:6, SEQ ID NO:7, a complement of SEQ ID NO:6 or a complement of SEQ ID NO:7) and probe (namely, SEQ ID NO:22 or a complement of SEQ ID NO:22) described previously herein in Section B.

Kits may also contain reagents for the isolation of nucleic acids from test samples prior to amplification before nucleic acid extraction.

The reagents may be supplied in a solid (e.g., lyophilized) or liquid form. Kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers are preferably maintained in close confinement for commercial sale.

Kits may also comprise instructions for using the amplification reagents and primer sets or primer and probe described herein: for processing the test sample, extracting nucleic acid molecules, and/or performing the test; and for interpreting the results obtained as well as a notice in the form prescribed by a governmental agency. Such instructions optionally can be in printed form or on CD, DVD, or other format of recorded media.

By way of example, and not of limitation, examples of the present disclosures shall now be given.

EXAMPLE 1

Materials and Methods

A. Design of HPV and Beta Globin Primers and Probes

All oligonucleotides used in Examples 2-6 were synthesized using standard oligonucleotide synthesis methodology known to those skilled in the art. All of the probes are single-stranded oligonucleotides labeled using routine techniques known in the art, with a fluorophore at the 5' end and a quenching moiety at the 3' end. The 5' label is a green label sold under VIC (this green label dye was used to label the probe specific for HPV 16 (namely, SEQ ID NO:8; See Table B in Section B)), a yellow label sold under NED (this yellow label was used to label the probe specific for HPV 18 (namely, SEQ ID NO:9; See Table B in Section B)), a blue label sold under FAM (this blue label dye was used to label probes specific HPV 31, 33, 35, 39, 45, 51, 52, 56, 58, 59, 66 or 68 (e.g., SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21; See Table B in Section B)), or a fluorescent label sold under QUASAR (for human beta globin; SEQ ID NO:22). The 3' label is a quencher (e.g., sold under BLACK HOLE QUENCHER or BHQ), such as the quencher sold under BHQ1-DT (used to label the probes specific for HPV 16, 31, 33, 35, 45, 51, 56, 59, 66 or 68; See Table B in Section B), the quencher sold under BHQ2-DT (used to label the probe specific for HPV18; see Table B in Section B), human beta globin (SEQ ID NO:22)) or the quencher sold under BHQ1 plus (used to label the probe specific for HPV 39, 52 or 58; See Table B in Section B).

B. Real-Time PCR

HPV DNA was extracted, concentrated and purified from samples using magnetic micro-particle technology that captures nucleic acids and washes the particles to remove unbound sample components (See, for example, U.S. Pat. No. 5,234,809). The bound nucleic acids were eluted and ready for amplification. A HPV primer mix of 3 forward primers (namely, SEQ ID NO:1, SEQ ID NO:2 and SEQ ID NO:3; See Table A in Section B) and 2 reverse primers (namely, SEQ ID NO:4 and SEQ ID NO:5; See Table A in Section B) targeting a conserved L1 region was used to amplify HPV targets. The 3 forward primers (SEQ ID NOS:1-3) and 2 reverse primers (SEQ ID NOS. 4-5) are collectively referred to herein as the "HPV Primer Mix". Signal for fourteen (14) human (HR) HPV genotypes (HPV 16, 18, 31, 33, 35, 39, 45, 51, 52, 56, 58, 59, 66, and 68) was generated with genotype specific probes (namely, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 and SEQ ID NO:21; See, Table B in Section B). All fourteen of these probes are collectively referred to herein as "HPV Probe Set"). Human beta globin target was amplified with a primer set (SEQ ID NOS:6 and 7) targeting an endogenous human beta globin sequence and detected with the beta globin probe (SEQ ID NO:22). Besides the primers and probes, the PCR reaction consisted of: 14 Units the DNA polymerase sold under AMPLITAQ GOLD, 7 mM magnesium chloride (as activation reagent) and other amplification reagents (containing 0.6 mM dNTPs, 73.5 nM ROX reference dye in Tris•buffer).

Real-time amplification/detection was carried out on an Abbott m2000rt instrument (Abbott Molecular Inc., Des Plaines, Ill.) using the following cycling conditions: 1 cycle at 92° C. 10 minutes; 4 cycles at 91° C. 30 seconds and 54° C. 30 seconds; 38 cycles at 91° C. 30 seconds, 52° C. 30 seconds (with 1 seconds per cycle auto-extension) and 50° C. 40 seconds. Fluorescence measurements were recorded during the read step (50° C.) of the 38 cycles.

EXAMPLE 2

Genotype Inclusivity and Partial Genotyping

In this Example, fifty-one (51) samples containing HPV DNA targets from each of the 14 genotypes were, individually and in combination, tested using the HPV Primer Mix and HPV Probe Set of Example 1. Real Time PCR was performed as described in Example 1. Each HPV DNA target was tested at a concentration of 400,000 copies per reaction. As shown below in Table 1, results from the 51 samples included 14 samples with a single genotype, 25 samples with two genotypes and 12 samples with three genotypes. As also shown in Table 1, these results were reported accurately and the presence or absence of HPV 16 and HPV 18 DNA was accurately determined in each case. This example demonstrates the capability of the unique HPV Primer Mix and HPV Probe Set to detect 14 HR HPV genotypes (HPV 16, 18, 31, 33, 35, 39, 45, 51, 52, 56, 58, 59, 66, and 68) and to distinguish HPV 16 and HPV 18 from the other 12 HR HPV genotypes.

TABLE 1

| Sample No. | HPV Genotype | Result |
|---|---|---|
| 1 | 16 | HPV 16 |
| 2 | 18 | HPV 18 |
| 3 | 31 | Other HR HPV |
| 4 | 33 | Other HR HPV |
| 5 | 35 | Other HR HPV |
| 6 | 39 | Other HR HPV |
| 7 | 45 | Other HR HPV |
| 8 | 51 | Other HR HPV |
| 9 | 52 | Other HR HPV |
| 10 | 56 | Other HR HPV |
| 11 | 58 | Other HR HPV |
| 12 | 59 | Other HR HPV |
| 13 | 66 | Other HR HPV |
| 14 | 68 | Other HR HPV |
| 15 | 16 + 18 | HPV 16; HPV 18 |
| 16 | 16 + 31 | HPV 16; Other HR HPV |
| 17 | 16 + 33 | HPV 16; Other HR HPV |
| 18 | 16 + 35 | HPV 16; Other HR HPV |
| 19 | 16 + 39 | HPV 16; Other HR HPV |
| 20 | 16 + 45 | HPV 16; Other HR HPV |
| 21 | 16 + 51 | HPV 16; Other HR HPV |
| 22 | 16 + 52 | HPV 16; Other HR HPV |
| 23 | 16 + 56 | HPV 16; Other HR HPV |
| 24 | 16 + 58 | HPV 16; Other HR HPV |
| 25 | 16 + 59 | HPV 16; Other HR HPV |
| 26 | 16 + 66 | HPV 16; Other HR HPV |
| 27 | 16 + 68 | HPV 16; Other HR HPV |
| 28 | 18 + 31 | HPV 18; Other HR HPV |
| 29 | 18 + 33 | HPV 18; Other HR HPV |
| 30 | 18 + 35 | HPV 18; Other HR HPV |
| 31 | 18 + 39 | HPV 18; Other HR HPV |
| 32 | 18 + 45 | HPV 18; Other HR HPV |
| 33 | 18 + 51 | HPV 18; Other HR HPV |
| 34 | 18 + 52 | HPV 18; Other HR HPV |
| 35 | 18 + 56 | HPV 18; Other HR HPV |
| 36 | 18 + 58 | HPV 18; Other HR HPV |

TABLE 1-continued

| Sample No. | HPV Genotype | Result |
|---|---|---|
| 37 | 18 + 59 | HPV 18; Other HR HPV |
| 38 | 18 + 66 | HPV 18; Other HR HPV |
| 39 | 18 + 68 | HPV 18; Other HR HPV |
| 40 | 16 + 18 + 31 | HPV 16; HPV 18; Other HR HPV |
| 41 | 16 + 18 + 33 | HPV 16; HPV 18; Other HR HPV |
| 42 | 16 + 18 + 35 | HPV 16; HPV 18; Other HR HPV |
| 43 | 16 + 18 + 39 | HPV 16; HPV 18; Other HR HPV |
| 44 | 16 + 18 + 45 | HPV 16; HPV 18; Other HR HPV |
| 45 | 16 + 18 + 51 | HPV 16; HPV 18; Other HR HPV |
| 46 | 16 + 18 + 52 | HPV 16; HPV 18; Other HR HPV |
| 47 | 16 + 18 + 56 | HPV 16; HPV 18; Other HR HPV |
| 48 | 16 + 18 + 58 | HPV 16; HPV 18; Other HR HPV |
| 49 | 16 + 18 + 59 | HPV 16; HPV 18; Other HR HPV |
| 50 | 16 + 18 + 66 | HPV 16; HPV 18; Other HR HPV |
| 51 | 16 + 18 + 68 | HPV 16; HPV 18; Other HR HPV |

EXAMPLE 3

Probe Hybridization Specificity

Two studies were used to demonstrate the hybridization specificity of the HPV Probe Set described in Example 1. Real-time PCR was performed as described in Example 1 with single HR HPV probes (See Table 2) or a cocktail containing all 14 HR HPV probes (See Table 3), in the presence of individual HPV plasmid DNA targets at a concentration of approximately 10,000,000 copies per reaction. The results of the two studies shown in Tables 2 and 3 demonstrate the specificity of the selected HPV probes.

TABLE 2

| | Target | Probe | | | | | | | | | | | | | |
|---|---|---|---|---|---|---|---|---|---|---|---|---|---|---|---|
| | | 16 | 18 | 31 | 33 | 35 | 39 | 45 | 51 | 52 | 56 | 58 | 59 | 66 | 68 |
| HR[1] | 16 (SEQ ID NO: 8) | + | − | − | − | − | − | − | − | − | − | − | − | − | − |
| HR | 18 (SEQ ID NO: 9) | − | + | − | − | − | − | − | − | − | − | − | − | − | − |
| HR | 31 (SEQ ID NO: 10) | − | − | + | − | − | − | − | − | − | − | − | − | − | − |
| HR | 33 (SEQ ID NO: 11) | − | − | − | + | − | − | − | − | − | − | − | − | − | − |
| HR | 35 (SEQ ID NO: 12) | − | − | − | − | + | − | − | − | − | − | − | − | − | − |
| HR | 39 (SEQ ID NO: 13) | − | − | − | − | − | + | − | − | − | − | − | − | − | − |
| HR | 45 (SEQ ID NO: 14) | − | − | − | − | − | − | + | − | − | − | − | − | − | − |
| HR | 51 (SEQ ID NO: 15) | − | − | − | − | − | − | − | + | − | − | − | − | − | − |
| HR | 52 (SEQ ID NO: 16) | − | − | − | − | − | − | − | − | + | − | − | − | − | − |
| HR | 56 (SEQ ID NO: 17) | − | − | − | − | − | − | − | − | − | + | − | − | − | − |
| HR | 58 (SEQ ID NO: 18) | − | − | − | − | − | − | − | − | − | − | + | − | − | − |
| HR | 59 (SEQ ID NO: 19) | − | − | − | − | − | − | − | − | − | − | − | + | − | − |
| HR | 66 (SEQ ID NO: 20) | − | − | − | − | − | − | − | − | − | − | − | − | + | − |
| HR | 68 (SEQ ID NO: 21) | − | − | − | − | − | − | − | − | − | − | − | − | − | + |
| LR[2] | 6 | − | − | − | − | − | − | − | − | − | − | − | − | − | − |
| LR | 11 | − | − | − | − | − | − | − | − | − | − | − | − | − | − |
| LR | 42 | − | − | − | − | − | − | − | − | − | − | − | − | − | − |
| LR | 43 | − | − | − | − | − | − | − | − | − | − | − | − | − | − |
| LR | 44 | − | − | − | − | − | − | − | − | − | − | − | − | − | − |

Note:
"+" designates HR HPV Detected;
"−" designates Not Detected.
[1]High Risk (HR)
[2]Low Risk (LR)

TABLE 3

| | Target | Result |
|---|---|---|
| LR | 6 | Not Detected |
| LR | 11 | Not Detected |
| LR | 13 | Not Detected |
| LR | 26 | Not Detected |
| LR | 30 | Not Detected |
| LR | 32 | Not Detected |
| LR | 40 | Not Detected |
| LR | 42 | Not Detected |
| LR | 43 | Not Detected |
| LR | 44 | Not Detected |
| LR | 53 | Not Detected |
| LR | 54 | Not Detected |
| LR | 55 | Not Detected |
| LR | 57 | Not Detected |
| LR | 61 | Not Detected |

EXAMPLE 4

Detection of Beta Globin as Cell Adequacy Control

In order for human beta globin to serve as a cell adequacy control, the beta globin signal, as in cycle number (CN) obtained from analysis of a real-time PCR result, should be indicative of the amount of cell input from clinical specimens.

A study was performed to evaluate the correlation between the amount of cells input from a cultured HPV positive cell line and beta globin signal. The correlation between the beta globin signal and amount of cells input is shown in FIG. 1. The study demonstrates that increase in the concentration of cells input correlates with higher beta globin detection efficiency as shown by earlier CN.

Additionally, a separate study was conducted to evaluate the beta globin CN distribution in clinical samples. A population of 1206 patient cervical specimens collected in a solution sold under PRESERVCYT (Cytyc Corporation, Marlborough, Mass.) was analyzed and shown in FIG. 2. The 25%, 50% and 75% quantile of the population has beta globin CN of 21.29, 22.41 and 23.78 respectively, with a minimum CN of 17.47 and a maximum CN of 36.01. This study demonstrates how beta globin can serve as a cell adequacy control.

Figure 2:
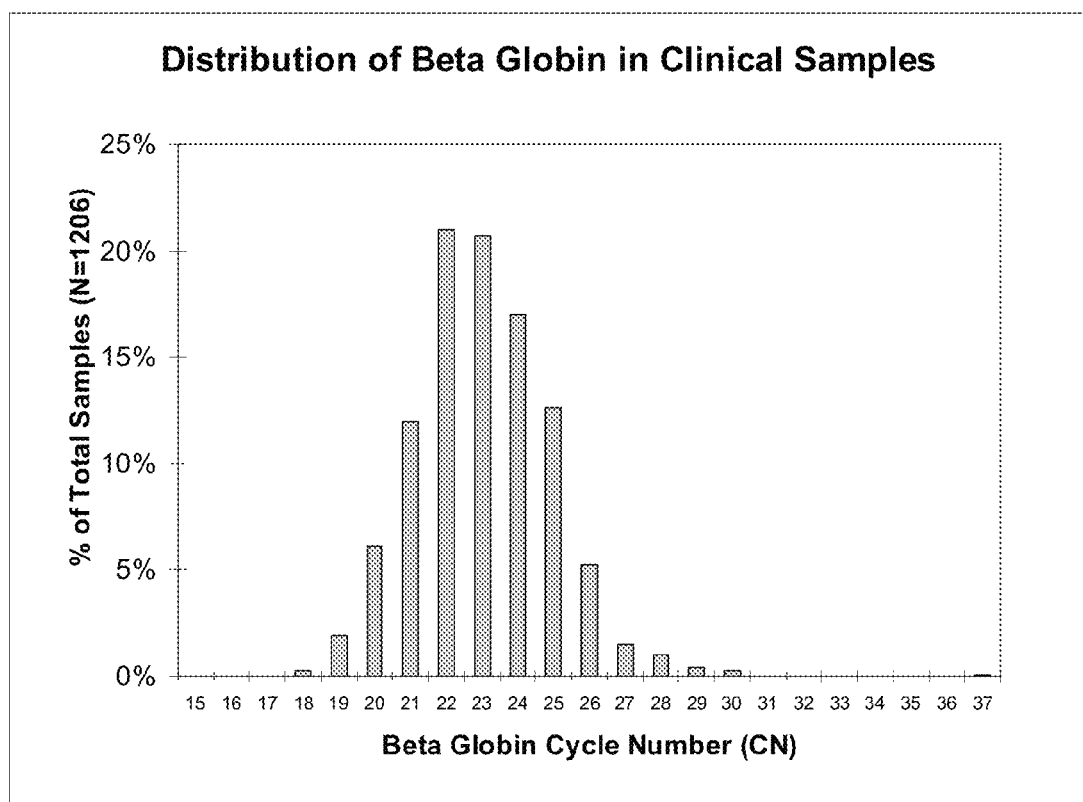
FIG. 2 shows the distribution of the beta globin cycle number for a population of 1206 patient cervical specimens as described in Example 4. Quantiles for the correlation described above in FIG. 1.
Figure 3A:
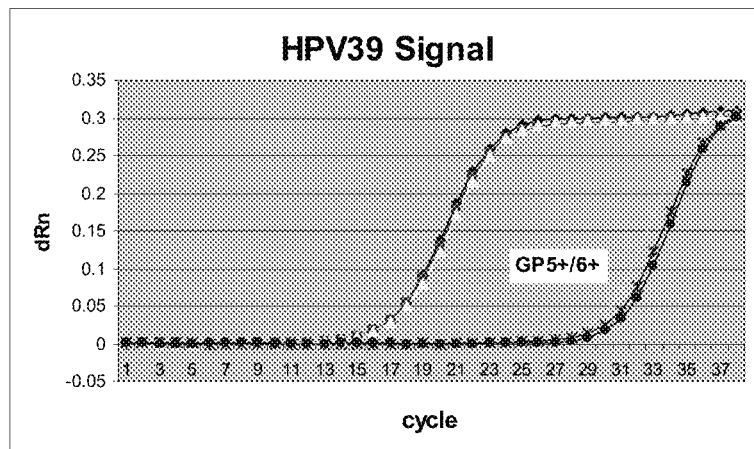
FIGS. 3A-3D shows a comparison of the analytical performance of a primer mix comprising SEQ ID NOS:1-5 to the GP5+ and GP6+ primers (SEQ ID NOS:23-24) as described in Example 5.
Figure 3B:
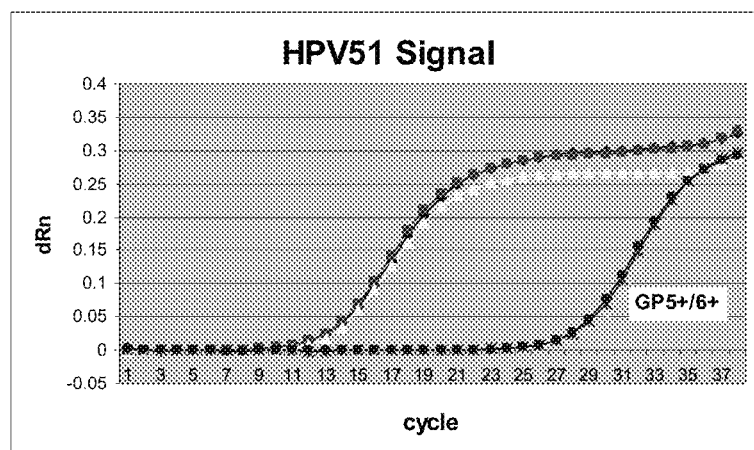
Figure 3C:
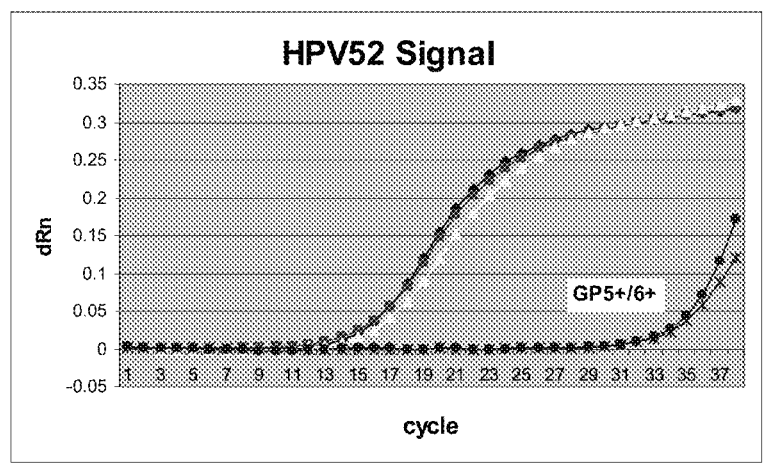
Figure 3D:
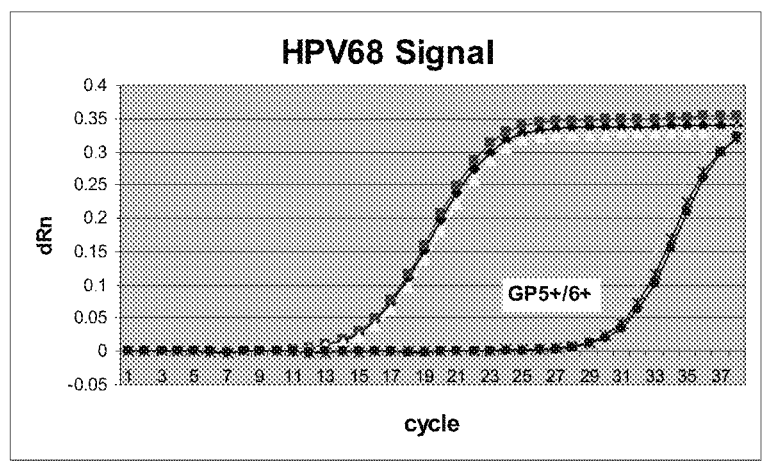
Figure 4A:
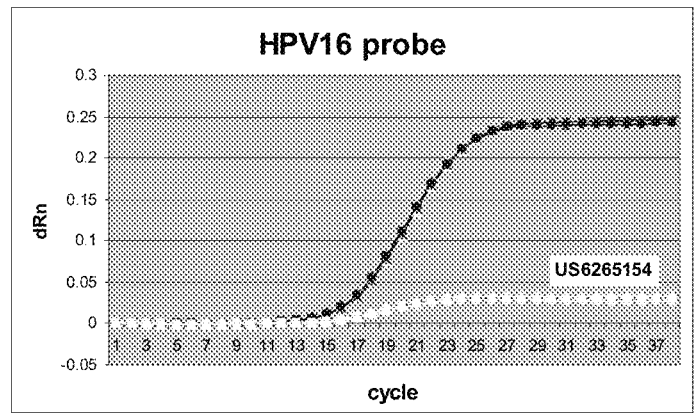
FIGS. 4A-4E shows a comparison of the analytical performance of a probes of the present invention specific for HPV types 16, 18, 31, 52 and 59 (SEQ ID NOS:8-10, 16 and 19) to the probe sequences for the same HPV types disclosed in U.S. Pat. No. 6,265,154B1 as described in Example 5.
Figure 4B:
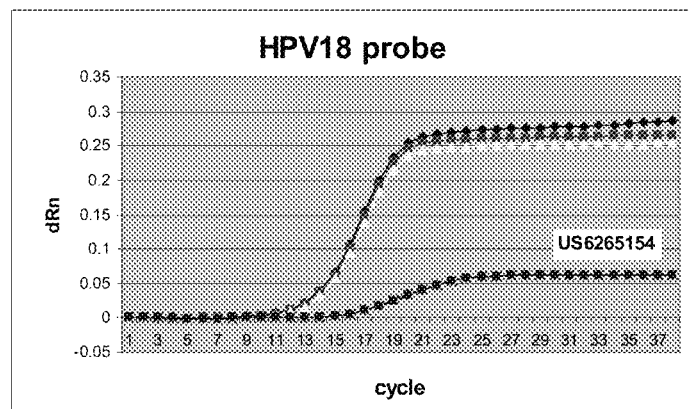
Figure 4C:
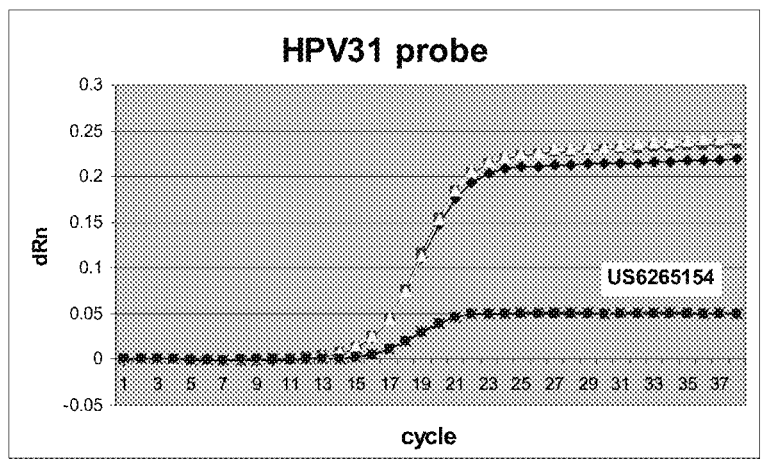
Figure 4D:
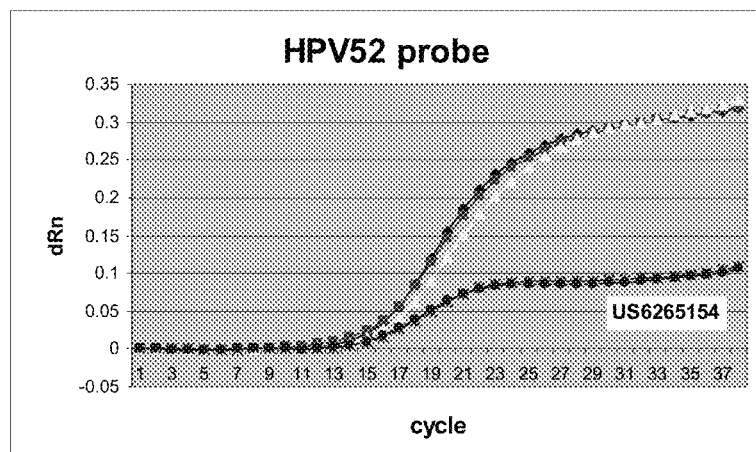
Figure 4E:
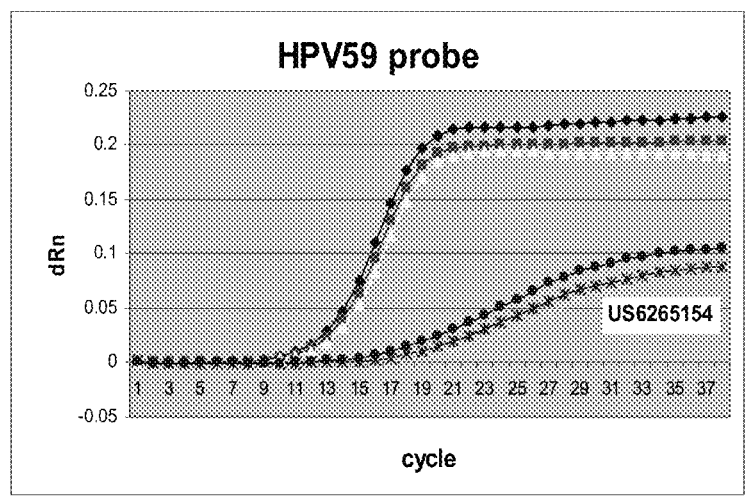

The human beta globin primers and probe as described in Example 1 were employed in Real Time PCR to generate the results shown in FIGS. 1 and 2.

EXAMPLE 5

Analytical Performance of the Primer and Probe Designs

This example describes the results of two studies. The first study demonstrated the improved analytical performance of the HPV Primer Mix of Example 1 when compared to the commonly used consensus GP5+/GP6+ primers (GP5+ primer: 5'-TTTGTTACTGTGGTAGATACTAC-3' (SEQ ID NO:23). GP6+ primer: 5'-GAAAAATAAACTGTAAAT-CATATTC-3' (SEQ ID NO:24)). This study was conducted using Real Time PCR as described in Example 1. The performance between the unique HPV Primer Mix of the present invention and the consensus GP5+/GP6+ primers was evaluated using CN values. The results are shown in Table 4 and FIGS. 3A-3D. Improvement in performance (CN improvement value>1) was observed for 10/13 HPV genotypes (Table 4). Major improvement was observed for HPV genotypes 39, 51, 52 and 68 (CN improvement value>10) and is shown in FIGS. 3A-3D.

TABLE 4

| HPV Genotype | SEQ ID NOS: 1-5 | GP5+/6+ Primers (SEQ ID NOS: 23-24) | CN Improvement of Claimed Sequences |
|---|---|---|---|
| 16 | 14.67 | 14.62 | −0.1 |
| 18 | 11.84 | 11.80 | 0.0 |
| 31 | 14.45 | 22.05 | 7.6 |
| 33 | 15.58 | 15.03 | −0.6 |
| 35 | 11.92 | 13.36 | 1.4 |
| 39 | 15.14 | 28.44 | 13.3 |
| 45 | 12.74 | 15.32 | 2.6 |
| 51 | 11.47 | 26.37 | 14.9 |
| 52 | 13.89 | 32.25 | 18.4 |
| 56 | 14.95 | 19.44 | 4.5 |
| 58 | 16.86 | 18.30 | 1.4 |
| 59 | 11.55 | 18.26 | 6.7 |
| 68 | 13.29 | 28.41 | 15.1 |

* Positive values indicate higher amplification efficiency in real-time PCR for the claimed sequences.

The second study examined the analytical performance of several of the unique probes of the present invention specific for HPV types 16, 18, 31, 35, 39, 45, 51, 52, 58 and 59 (SEQ ID NOS: 8-10, 12-16 and 18-19) compared to the probe sequences for the same HPV types disclosed in U.S. Pat. No. 6,265,154 B1 (See Table 5). The probes of U.S. Pat. No. 6,265,154 were labeled as described in Example 1 in order to allow a direct comparison when tested in Real-Time PCR. The performance was evaluated using CN values and fluorescence signals. The results are shown in Table 6, Table 7 and FIGS. 4A-4E. Improvement in performances (CN improvement value >1 and fluorescence signal >0.1) was observed for 5/10 HPV genotypes (Table 6 and Table 7). The significant improvement in CN and fluorescence signals was observed for HPV genotypes 16, 18, 31, 52 and 59 and is shown in FIGS. 4A-4E.

TABLE 5

| SEQ ID NO. from U.S. Pat. No. 6,265,154 | HPV Specificity |
|---|---|
| 4 | 16 |
| 7 | 18 |
| 10 | 31 |
| 16 | 35 |
| 19 | 39 |
| 22 | 45 |
| 25 | 51 |
| 28 | 52 |
| 34 | 58/33 |
| 37 | 59 |

TABLE 6

| HPV Genotype | Sequences of the present invention | Sequence in U.S. Pat. No. 6,265,154 | CN Improvement of Claimed Sequence* |
|---|---|---|---|
| 16 | 14.59 (SEQ ID NO: 8) | 17.59 (SEQ ID NO: 4) | 3.0 |
| 18 | 11.84 (SEQ ID NO: 9) | 16.88 (SEQ ID NO: 7) | 5.0 |
| 31 | 14.45 (SEQ IDNO: 10) | 16.79 (SEQ ID NO: 10) | 2.3 |

TABLE 6-continued

| HPV Genotype | Sequences of the present invention | Sequence in U.S. Pat. No. 6,265,154 | CN Improvement of Claimed Sequence* |
|---|---|---|---|
| 35 | 11.92 (SEQ ID NO: 12) | 11.99 (SEQ ID NO: 16) | 0.1 |
| 39 | 15.14 (SEQ IDNO: 13) | 15.57 (SEQ ID NO: 19) | 0.4 |
| 45 | 12.74 (SEQ IDNO: 14) | 13.36 (SEQ ID NO: 22) | 0.6 |
| 51 | 11.47 (SEQ ID NO: 15) | 10.71 (SEQ ID NO: 25) | −0.8 |
| 52 | 13.89 (SEQ ID NO: 16) | 14.99 (SEQ ID NO: 28) | 1.1 |
| 58 | 16.86 (SEQ ID NO: 18) | 16.25 (SEQ ID NO: 34) | −0.6 |
| 59 | 11.55 (SEQ ID NO: 19) | 18.69 (SEQ ID NO: 37) | 7.1 |

*Positive values indicate higher detection efficiency in real-time PCR of the claimed sequences.

TABLE 7

| HPV Genotype | Sequences of the present invention | Sequence in U.S. Pat. No. 6,265,154 | Fluorescence Signal Improvement of Claimed Sequence |
|---|---|---|---|
| 16 | 0.153 (SEQ ID NO: 8) | 0.028 (SEQ ID NO: 4) | 0.125 |
| 18 | 0.265 (SEQ ID NO: 9) | 0.062 (SEQ ID NO: 7) | 0.203 |
| 31 | 0.235 (SEQ IDNO: 10) | 0.051 (SEQ ID NO: 10) | 0.184 |
| 35 | 0.220 (SEQ ID NO: 12) | 0.280 (SEQ ID NO: 16) | −0.060 |
| 39 | 0.301 (SEQ IDNO: 13) | 0.522 (SEQ ID NO: 19) | −0.221 |
| 45 | 0.234 (SEQ IDNO: 14) | 0.279 (SEQ ID NO: 22) | −0.045 |
| 51 | 0.317 (SEQ ID NO: 15) | 0.295 (SEQ ID NO: 25) | 0.022 |
| 52 | 0.316 (SEQ ID NO: 16) | 0.103 (SEQ ID NO: 28) | 0.213 |
| 58 | 0.365 (SEQ ID NO: 18) | 0.469 (SEQ ID NO: 34) | −0.104 |
| 59 | 0.204 (SEQ ID NO: 19) | 0.088 (SEQ ID NO: 37) | 0.116 |

EXAMPLE 6

Clinical Performance of the Primer and Probes of the Present Invention

The sensitivity and specificity of an assay using the HPV Primer Mix and HPV Probe Set as described in Example 1 for detection of HR HPV were evaluated by testing 441 patient cervical specimens collected in the solution sold under PRE-SERVCYT (Cytyc Corporation, Marlborough, Mass.). The high risk HPV status of cervical specimens was determined by the concordance between the Abbott RealTime HR HPV assay (Abbott Laboratories, Abbott Park, Ill.) and hc2 High-Risk HPV DNA Test ("HC2") (commercially available from Qiagen, Inc., Valencia, Calif.) tests and by further analysis of specimens with discordant results using the LINEAR ARRAY HPV Genotyping Test (commercially available from Roche Diagnostics, Basel, CH; "Linear Array"). All three of these assays or tests were conducted pursuant to the manufacturer's instructions. A total of 227 specimens were detected by both assays and 179 were not detected by either assay. The results of 35 discordant specimens were resolved by Linear Array. Of the 238 positive specimens, 231 were detected by the Abbott RealTime HR HPV assay and 234 were detected by HC2. Of the 203 resolved negative specimens, 203 were not detected by the Abbott RealTime HR HPV assay and 179 were not detected by HC2. As shown below in Table 8, the sensitivity of the Abbott RealTime HR HPV assay for detection of HR HPV was 97% and of HC2 assay was 98%. The specificity of the Abbott RealTime HR HPV assay was 100% and of HC2 assay was 88%.

TABLE 8

| Test | Sensitivity | Specificity |
|---|---|---|
| Abbott RealTime HR HPV | 97% | 100% |
| HC2 | 98% | 88% |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments. Optional features, modifications and variations of the concepts herein disclosed may be resorted to by those skilled in the art and such modifications and variations are considered to be within the scope of this invention as defined by the appended claims.

What is claimed is:

1. A set of polynucleotides for detecting HPV types 16, 18, 31, 35, 39, 45, 51, 52, 58, 59, and 66 in a test sample, wherein the polynucleotides comprise:
   (a) three different isolated forward primers and two different isolated reverse primers,
      (i) wherein each isolated forward primer consists of a sequence selected from the group consisting of: SEQ ID NO:1, SEQ ID NO:2, SEQ ID NO:3, and full-length complements thereof;
      (ii) wherein each isolated reverse primer consists of a sequence selected from the group consisting of: SEQ ID NO:4 and SEQ ID NO:5, and full-length complements thereof; and
   (b) eleven different isolated probes, wherein each probe consists of a sequence selected from the group consisting of: SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:18, SEQ ID NO:19, SEQ ID NO:20, and full-length complements thereof, wherein each probe is labeled with a detectable label; wherein the detectable label comprises a fluorescent moiety attached at the 5' end of the probe.

2. A primer and probe kit for detecting HPV types 16, 18, 31, 35, 39, 45, 51, 52, 58, 59, and 66 in a test sample, wherein said kit comprises:
   (a) three different isolated forward primers and two different isolated reverse primers,
      (i) wherein each isolated forward primer consists of a sequence selected from the group consisting of: SEQ ID NO:1, SEQ ID NO:2 and SEQ ID NO:3 and full-length complements thereof;
      (ii) wherein each isolated reverse primer consists of a sequence selected from the group consisting of: SEQ ID NO:4, SEQ ID NO:5 and full-length complements thereof;
   (b) eleven different isolated probes, wherein each isolated probe consists of a sequence selected from the group consisting of: SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:18, SEQ ID NO:19, SEQ ID NO:20, and full-length complements thereof, wherein each probe is labeled with a detectable label; wherein the detectable label comprises a fluorescent moiety attached at the 5' end of the probe;

(c) amplification reagents.

3. The primer and probe kit of claim 2, wherein the kit further comprises an isolated forward primer consisting of SEQ ID NO:6 or a complement thereof, wherein the complement is identical in length to SEQ ID NO:6, an isolated reverse primer consisting of SEQ ID NO:7 or a complement thereof, wherein the complement is identical in length to SEQ ID NO:7, and an isolated probe consisting of SEQ ID NO:22 or a complement thereof, wherein the complement is identical in length to SEQ ID NO:22, for detecting human beta globin in a test sample.

4. The set of polynucleotides of claim 1, wherein each probe further comprises a quencher moiety attached at its 3' end.

5. The primer and probe kit of claim 2, wherein each probe further comprises a quencher moiety attached at its 3' end.

* * * * *